US012427203B2

(12) United States Patent
Liu et al.

(10) Patent No.: US 12,427,203 B2
(45) Date of Patent: *Sep. 30, 2025

(54) LONG ACTING MULTI-SPECIFIC MOLECULES AND RELATED METHODS

(71) Applicant: SHENZHEN ENDURING BIOTECH, LTD., Shenzhen (CN)

(72) Inventors: Shu-min Liu, Monmouth Junction, NJ (US); Dechun Wu, Bridgewater, NJ (US)

(73) Assignee: Shenzhen Enduring Biotech, Ltd., Shenzhen (CN)

( * ) Notice: Subject to any disclaimer, the term of this patent is extended or adjusted under 35 U.S.C. 154(b) by 994 days.

This patent is subject to a terminal disclaimer.

(21) Appl. No.: 17/373,296

(22) Filed: Jul. 12, 2021

(65) Prior Publication Data
US 2021/0338832 A1 Nov. 4, 2021

Related U.S. Application Data

(63) Continuation of application No. 16/341,486, filed as application No. PCT/US2017/056118 on Oct. 11, 2017, now Pat. No. 11,065,342.

(60) Provisional application No. 62/408,865, filed on Oct. 17, 2016.

(51) Int. Cl.
| | |
|---|---|
| A61K 47/68 | (2017.01) |
| A61K 47/60 | (2017.01) |
| C07K 16/28 | (2006.01) |
| C07K 16/46 | (2006.01) |
| A61K 39/00 | (2006.01) |

(52) U.S. Cl.
CPC .......... *A61K 47/6881* (2017.08); *A61K 47/60* (2017.08); *A61K 47/6801* (2017.08); *A61K 47/6849* (2017.08); *A61K 47/6851* (2017.08); *C07K 16/2803* (2013.01); *C07K 16/2809* (2013.01); *C07K 16/468* (2013.01);
(Continued)

(58) Field of Classification Search
CPC ................ A61K 47/60; A61K 47/6801; A61K 47/6851; A61K 47/6835; A61K 47/6881; C07K 16/2803; C07K 16/2809
See application file for complete search history.

(56) References Cited

U.S. PATENT DOCUMENTS

| 11,065,342 B2 * | 7/2021 | Liu ..................... C07K 16/2809 |
| 2004/0018203 A1 * | 1/2004 | Pastan ................ C07K 16/2866 |
| | | 424/1.49 |

(Continued)

FOREIGN PATENT DOCUMENTS

| AU | 2014273052 A1 * | 1/2016 | ............. A61P 35/02 |
| JP | 2019537572 A | 12/2019 | |

(Continued)

OTHER PUBLICATIONS

Florinas, S. et al., "A Nanoparticle Platform To Evaluate Bioconjugation and Receptor-Mediated Cell Uptake Using Cross-Linked Polyion Complex Micelles Bearing Antibody Fragments"; Biomacromolecules (2016); vol. 17(5); pp. 1818-1833.

(Continued)

*Primary Examiner* — Rayna Rodriguez
*Assistant Examiner* — Janet L Coppins
(74) *Attorney, Agent, or Firm* — Fox Rothschild LLP

(57) ABSTRACT

This invention relates to multi-specific molecules, such as long acting multi-specific antibodies. Also disclosed are related methods.

14 Claims, 6 Drawing Sheets

Specification includes a Sequence Listing.

(52) U.S. Cl.
CPC .... *A61K 2039/505* (2013.01); *C07K 2317/31* (2013.01); *C07K 2317/622* (2013.01); *C07K 2317/94* (2013.01)

(56) References Cited

U.S. PATENT DOCUMENTS

| | | | |
|---|---|---|---|
| 2015/0225484 A1* | 8/2015 | Little | C07K 16/2803 530/387.3 |
| 2015/0328314 A1* | 11/2015 | Friedman | A61N 5/062 530/304 |
| 2021/0338832 A1 | 11/2021 | Liu et al. | |

FOREIGN PATENT DOCUMENTS

| | | |
|---|---|---|
| WO | 2013033476 A1 | 3/2013 |
| WO | 2015175357 A9 | 11/2015 |

OTHER PUBLICATIONS

Portell et al., "Clinical and Pharmacologic aspects of Blinatumomab in the Treatment of B-cell Acute Lymphoblastic Leukemia"; Clinical Pharmacology: Advances and Applications (2011); 3:5(Suppl 1):5-11.

Kim, T. H. et al., "Mono-PEGylated Dimeric Exendin-4 as High Receptor Binding and Long-Acting Conjugates for Type Anti-Diabetes Therapeutics"; Bioconjugate Chemistry (2011); vol. 22:4; pp. 625-632.

\* cited by examiner

LONG ACTING MULTI-SPECIFIC MOLECULES AND RELATED METHODS

CROSS REFERENCE TO RELATED APPLICATION

This application is a continuation of U.S. application Ser. No. 16/341,486, filed Apr. 12, 2019, which is a 371 of International Patent Application No.: PCT/US2017/056118, filed Oct. 11, 2017, which claims the benefit of priority to U.S. Provisional Application No. 62/408,865 filed on Oct. 17, 2016. The contents of the applications are incorporated herein by reference in their entirety.

FIELD OF THE INVENTION

This invention generally relates to multi-specific molecules and, in particular, relates to long acting multi-specific antibodies and to methods of making and using long acting multi-specific binding molecules.

BACKGROUND OF THE INVENTION

A multi-specific molecule, e.g., a bispecific monoclonal antibody (BsAb), is an artificial protein or conjugate that is composed of two or more different molecules (such as monoclonal antibodies or antigen binding portions thereof). A bispecific antibody binds to two different types of targets (e.g., antigens) and can be used to treat certain disorders. The clinical development of bispecific antibodies started in early 90's (Canevari, S. et al. 1995, J. Hematother 4, 423-427; Valone, F. H. et al. 1995, J. Clin. Oncol. 13, 2281-2292). Not until a decade later, the first bispecific antibody "Catumaxomab" (trade name Removab) was approved for commercial use in Europe by European Medicines Agency (EMA) in 2009. Second bispecific antibody "Blinatumomab" (trade name Blincyto) was approved by US FDA in 2014. Bispecific antibodies have been made via quadroma technology based on the somatic fusion of two different hybridoma cell lines (Milstein, C. et al. 1983, Nature, 305(5934): p. 537-40) or chemical conjugation of two different monoclonal antibodies or antibody fragments (Brennan, M., et al., 1985 Science, 229(4708): p. 81-3; Glennie, M. J., et al., 1987 J Immunol, 139(7): p. 2367-75) or recently recombinant and fusion technology. However, the challenges of manufacturing recombinant bispecific antibodies have been huge hurdles to bring such promising therapeutics to patients (Klein C. et al. 2012, MAbs. 4(6): 653-663). Moreover, the short half-lives of some of these molecules have also severely limited their further advancement to clinics. Furthermore, in some disease applications, such as solid tumor application, some of these molecules either are too big for deep penetration into tumor tissue or have limited retention time in the tumor tissue (Thurber, G. M. et al., 2007, J. Nuclear Medicine. 48(6): 995-999; Minchinton, A. I. et al. 2006, Nature Reviews Cancer. 6: 583-592), which results in inferior outcomes of the treatments. Therefore, there is a need for novel long acting bispecific molecules and related preparation methods.

SUMMARY OF INVENTION

This invention addresses the aforementioned unmet need by providing multi-specific molecules and related methods.

In one aspect, the invention provides a multi-specific molecule, conjugate, or compound of the Formula Ia

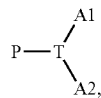

wherein P is a non-immunogenic polymer; T is a trifunctional small molecule linker moiety and has one, two, or more functional groups that are capable of site-specific conjugation with two different proteins; and A1 and A2 are any two different or same proteins.

In particular, an aspect of the invention provides a conjugate of Formula Ib:

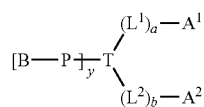

Formula Ib
wherein:
P is a non-immunogenic polymer;
B is H, a terminal capping group or void, said capping group selected from $C_{1-50}$ alkyl and aryl, wherein one or more carbons of said alkyl may be replaced with a heteroatom;
T is a multi-functional linker having one, two, or more functional groups, wherein the linkage between T and $(L^1)_a$ and the linkage between T and $(L^2)_b$ could be same or different;
each of $L^1$ and $L^2$ are independently a bifunctional linker;
a and b are each an integer selected from 0-10;
$A^1$ and $A^2$ can be any two different or same proteins. For example, $A^1$ and $A^2$ are different from each other and each of $A^1$ and $A^2$ independently comprises an antibody fragment, single chain antibody, or any other antigen binding potion or combination thereof; or $A^1$ and $A^2$ are the same and both are multispecific antigen binding protein; and
y is an integer selected from 1-10.

At least one of the proteins comprises a recognition binding moiety. For example, $A^1$ comprises a first recognition binding moiety and $A^2$ comprises a second recognition binding moiety. The two different proteins can be two different antibodies or antigen-binding portions thereof. In one example, the two antibodies are respectively an anti-CD3 antibody that binds to a receptor on cytotoxic cell and an anti-CD19 antibody that binds to a receptor of cancer cell. The two antibodies can be single chain antibodies (SCA or scFv).

The non-immunogenic polymer can be selected from the group consisting of polyethylene glycol (PEG), dextrans, carbohydrate-base polymers, polyalkylene oxide, polyvinyl alcohols, hydroxypropyl-methacrylamide (HPMA), and a co-polymer thereof. Preferably, the non-immunogenic polymer is PEG, such as a branched PEG or a linear PEG or a multi-arm PEG. In that case, at least one terminal of linear PEG or branch PEG is capped with H, methyl or low molecule weight alkyl group. The total molecule weight of the PEG can be 3,000 to 100,000, e.g., 5,000 to 80,000, 10,000 to 60,000, and 20,000 to 40,000. The PEG can be linked to a multifunctional moiety either through a permanent bond or a cleavable bond.

The functional groups (e.g., two site-specific conjugation functional groups) that form linkages within $(L^1)_a$ or $(L^2)_b$ or between $(L^1)_a$ and protein $A^1$ or between $(L^2)_b$ and protein $A^2$ can be selected from the group consisting of thiol, maleimide, 2-pyridyldithio variant, aromatic sulfone or vinyl sulfone, acrylate, bromo or iodo acetamide, azide, alkyne, dibenzocyclooctyl (DBCO), carbonyl, 2-amino-benzaldehyde or 2-amino-acetophenone group, hydrazide, oxime, potassium acyltrifluoroborate, O-carbamoylhydroxylamine, trans-cyclooctene, tetrazine, triarylphosphine, etc.

In some embodiments, one of $(L^1)_a$ and $(L^2)_b$ can comprise a linkage formed from azide and alkyne. The other of the $(L^1)_a$ and $(L^2)_b$ can comprise a linkage formed from maleimide and thiol. In some examples, the alkyne can be dibenzocyclooctyl (DBCO). In others, T is lysine, P is PEG, and y is 1, while the alkyne is dibenzocyclooctyl (DBCO). In some embodiments, one of $A^1$ and $A^2$ can be derived from an azide tagged antibody, antibody chain, antibody fragment, or single chain antibody, wherein the azide is conjugated to an alkyne in the respective $(L^1)_a$ or $(L^2)_b$; the other of $A^1$ and $A^2$ can be derived from a thiol tagged antibody, antibody chain, antibody fragment or single chain antibody, wherein the thiol is conjugated to a maleimide in the respective $(L^1)_a$ or $(L^2)_b$.

The above-described multi-specific molecule or compound can be made according to a method comprising: (i) preparing a non-immunogenic polymer with terminal bi-functional groups capable of site-specific conjugation with two different proteins or their modified forms; and (ii) stepwise site-specific conjugating the non-immunogenic polymer with two different proteins or their modified forms to form a compound of Formula Ia or Ib. In some examples, before the preparing step, the proteins can be modified with a small molecule linker first.

The invention also provides a pharmaceutical formulation comprising the multi-specific molecule or compound described above and a pharmaceutically acceptable carrier. The invention further provides a method of treating a disease in a subject in need thereof comprising administering an effective amount of the multi-specific molecule or compound described above.

The details of one or more embodiments of the invention are set forth in the description below. Other features, objectives, and advantages of the invention will be apparent from the description and from the claims.

DETAILED DESCRIPTION OF THE INVENTION

Figure 1A:
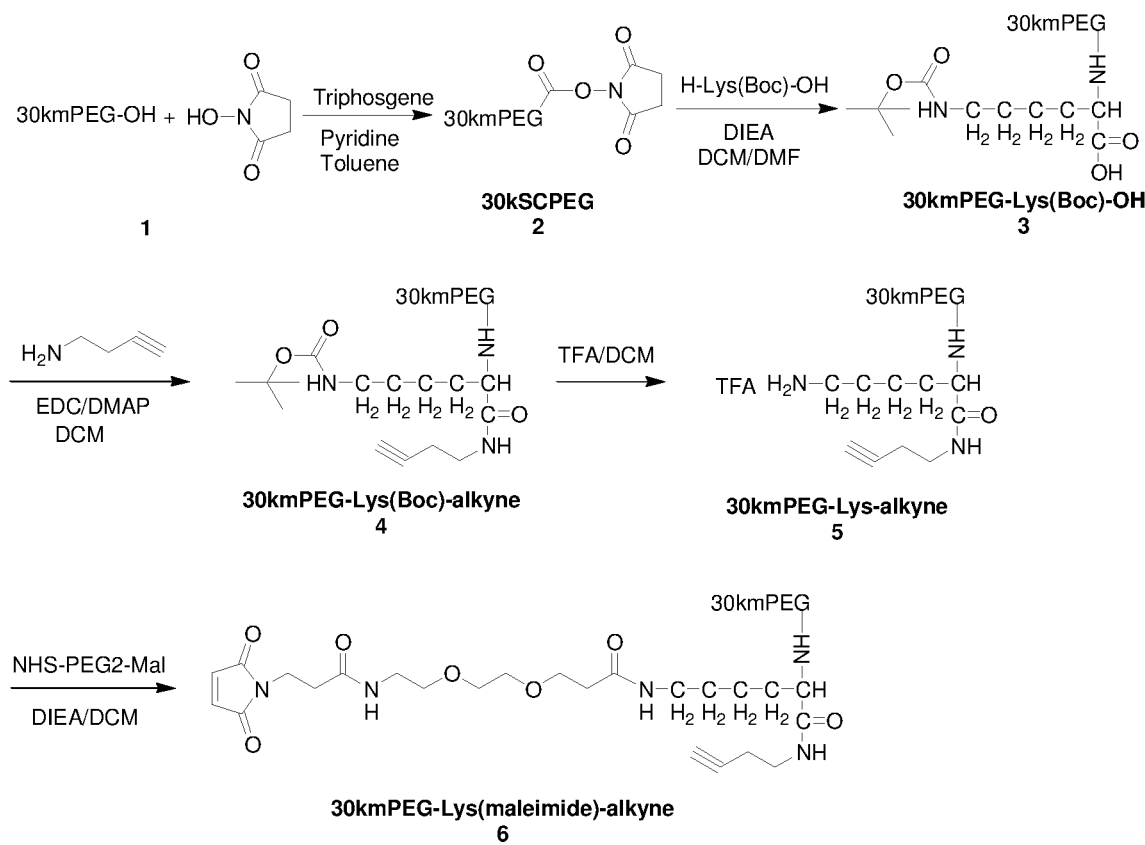
FIG. 1A schematically illustrates a reaction scheme of preparing 30 kmPEG-Lys(maleimide)-alkyne described in Example 1 (compounds 2, 3, 4, 5, 6).

This invention relates to novel long acting multi-specific molecules (e.g., multi-specific or bispecific antibodies) and related methods of making and using such molecules. In particular, the multi-specific molecules provided herein are Double Site-specific PEGylated Bispecific Antibody (DSP-BsAb), and are capable of binding two or more antigens, or two or more epitopes of the same antigen.

A bispecific monoclonal antibody (BsAb) is an artificial protein that comprises antigen-binding fragments of two different monoclonal antibodies. It binds to two different types of antigen or two different epitopes of the same antigen. The most widely used application of this approach is in cancer immunotherapy, where an engineered BsAb binds both to a receptor of cytotoxic cell, e.g., CD3, and a receptor of cancer cell, e.g., CD19, and redirect cytotoxic cell, e.g. T cell, to destroy the cancer cells. For example, among the onco-immunotherapies, Blinatumomab, a Bi-specific T-cell engager (BiTE) developed by Amgen, is one of the most successful therapies developed.

Blinatumomab is a bispecific fusion antibody for treatment of cancer. It is made up of two single-chain monoclonal antibodies that bind specifically to CD19 and CD3 respectively to redirect effector T cells to kill CD19 positive B cancer cells. However, similar to other recombinant antibody fragment proteins, Blinatumomab is cleared very quickly during blood circulation and must be administered by a continuous intravenous infusion 24 hours a day, 7 days a week with a portable mini-pump (Portell, C. A. et al., 2013, Clin Pharmacol, 5 (Suppl 1): p. 5-11). This special drug administration has been a great challenge for patients to comply with, particularly for young children. Additionally, high chance of infection has put these patients at a great risk and in worst case even to death. Moreover, due to their extremely short half life, fused single chain bispecific antibodies like Blinatumomab typically have very poor retention time in solid tumor; therefore, likelihood of success in redirecting effector cells to destroy the solid tumors is very questionable. Furthermore, Blinatumomab administered with bolus injection can result in substantial central nervous system (CNS) toxicities possibly due to leakage of antibody into to the brain (Ahmed, M. et al. April 2015, Onco Immunology 4 (4)) e989776-1-e989776-11). To address those problems, we disclose here a novel bispecific antibody technology—DSP-BsAb technology.

Chemical conjugation of two antibodies or antibody fragments to form BsAb had been reported in past prior to the advent of recombinant fusion methods. Indeed, the first reported BsAbs were BsF(ab')$_2$ obtained by pepsin digestion of two rabbit IgG followed by reduction and then reoxidation of the resulting Fab' fragments. More efficient production of BsF(ab')$_2$ fragments was achieved using cysteine-reactive homo- and hetero-bifunctional cross linking reagents (Brennan, M. et al. 1985, Science 229 (4708): 81-83, Glennie, M. J. et al. 1987, J Immunol 139 (7): 2367-2375, S. SONGSIVILAI & P. J. LACHMANN. Clin. exp. 1990, Immunol. 79, 315-321), or through direct conjugation between two recombinant expressed Fab' fragments (Shalaby M. R. et al. 1992, J Exp Med 175(1): 217-225). Although a number of methods have been described to chemically make bispecific antibodies using antibody fragments (Fabs, or scFvs), many of these approaches, however, present a variety of problems, e.g. low conjugation yield and purity or difficulty with large scale production.

Today the advancement of molecular biology has made it possible that almost, if not all, any pair of antibody fragments or chains can been integrated technically into a bispecific antibody molecule. However, the challenges of manufacturing recombinant fused bispecific antibodies have been huge hurdles (Klein C. et al. 2012, MAbs. 4(6): 653-663.) for clinical development. Furthermore, the short half-life of these promising molecules has also severely limited their further advancement into clinics.

Since its invention in the 1970s, PEGylation, as one of the most successful protein modification strategies, has been used extensively in pharmaceutical industry (Jevšever, S., M. et al., 2010, Biotechnology Journal, 5(1): p. 113-128; Veronese, F. BioDrugs, 22(5): p. 315-329). The conjugation of PEG with therapeutic molecules such as proteins and polypeptides to extend their circulation half-life and improve their pharmacokinetics and pharmacodynamics is well known (U.S. Pat. No. 4,179,337).

There are two possible formats of PEGylated bispecific antibody when a linear PEG is used; one with two different antibodies or antigen-binding portions attached at both terminals of a linear PEG (format I) and the other with two different antibodies or antigen-binding portions attached only at one terminal of a PEG (format II). Depending on specific application, one format could be chosen preferably over the other. In the case of combinational therapy for synergistic effect, choice of one format over another might not seem to be critical, but in the case of recruiting cytotoxic effector cells to kill the cancer cell, the format with two different antibodies or antigen-binding portions attached at both terminals of a PEG (format I) is inferior due to at least following two reasons. First, the close proximity of target cell to effector cell is crucial for the formation of the immunological synapse to effectively redirect effector cells for direct lysis (Wuellner, U. et. al., 2015, Antibodies, 4, p. 426-440; Bluemel, C. et. al., 2010, Cancer Immunol Immunother. 59(8):p. 1197-209), in other words, two different antibodies or antigen-binding portions of a bispecific antibody should be very close to each other for onco-immunotherapy to work effectively, but the format I of PEGylated bispecific antibody has no mechanism to control spatial distance between two different antigen-binding moieties, therefore cannot fulfill this distance requirement. Second, PEG chain in this format is not able to move freely to fully utilize its potential to protect antigen-binding moieties that typically have short elimination half-life. The right approach is to construct PEGylated bispecific antibody (Format II) with two different antibodies or antigen-binding portions attached at only one terminal of PEG as disclosed in this invention, leaving the other terminal (in the case of a linear PEG) or terminals (in the case of branch or mulri-arm PEG) of PEG free so that PEG can protect short-lived bispecific antibody more efficiently. With this structure format (Format II), a required immunological synapse is also provided for effectively retargeting effector cells to kill the cancer cells. Therefore, better pharmacokinetics and better pharmacodynamics could be expected.

To site-specifically conjugate two different antibody fragments or single chain antibodies at one PEG terminal to form a PEGylated bispecific antibody, a terminal functional groups of PEG, such as hydroxyl group, carboxyl group etc., must be converted to terminal branched heterobifunctional groups, which are capable of site-specific conjugations with two antibody fragments or single chain antibodies. Methods for preparing terminal branched PEG have been disclosed in U.S. Pat. Nos. 6,756,037, 6,638,499, and 6,777,387, but none of disclosed terminal branched PEGs in those patents are capable of performing site specific conjugation with two different antibody fragments or single chain antibodies or other formats of antigen-binding potions.

Conceptually PEGylated bispecific antibody can be prepared by attaching a PEG to a fused bispecific antibody. The problem with this approach is that manufacturing a fused antibody is much more challenging and difficult technically than manufacturing a single antibody fragment or a single chain antibody. An alternative approach disclosed in this invention is manufacturing two different antibody fragments or single chain antibodies separately and then linking these two antibody fragments or single chain antibodies chemically with a PEG with a tri-functional small molecule moiety in between.

There are two approaches that can be used to chemically link two different antibody fragments or single chain antibodies to a PEG to form a PEGylated bispecific antibody. The first approach is to site-specifically link two different antibody fragments or single chain antibodies first followed by site-specific PEGylation. The problem with this approach lies in the coupling of two different antibody fragments or single chain antibodies. It turns out that the coupling process typically is much challenging in term of identifications and purifications simply due to the tendency of dimer (e.g., $(scFv1)_2$ and $(scFv2)_2$) formation of such antibody fragments or single chain antibodies, which often have similar molecule weight and physical characteristics to the target compounds (e.g., scFv1-scFv2).

The other approach is using DSP-BsAb technology disclosed in this invention. With DSP-BsAb technology, one can site-specifically PEGylate one antibody fragment or single chain antibody first followed by site-specific conjugation with another antibody fragment or single chain antibody. Because PEGylated antibody fragment or PEGylated single chain antibody has very different characteristics from the antibody fragment or single chain antibody or their dimers, with this approach, the purification and characterization process could be much easy.

This invention provides a method of preparing terminal branched PEG that is capable of site-specific conjugation with two different antibody fragments or single chain antibodies such as anti-CD19 and anti-CD3. As disclosed herein, blood circulation half-life for the bispecific antibody can be improved. In addition, conventional single-specific/mono-specific antibody fragments, single chain antibodies, or antigen-binding portions thereof can be used for manufacturing bispecific antibodies of this invention, which means easy manufacturing process as compared with manufacturing of recombined fused bispecific antibody. Moreover, disclosed PEGylated bispecific antibody format has the advantages of recruiting effector cells to kill the cancer cells for onco-immunotherapy. Furthermore, since traditional full length bispecific antibodies or any of their derivatives are usually too big for deep penetration into the solid tumor tissues while traditional single chain bispecific antibodies or antibody fragments or any of their derivatives have limited retention time in solid tumor tissues, DSP-BsAb technology disclosed herein has the ability to balance the size and circulation half life of the bispecific antibody and potentially provide more effective treatment for solid tumor.

Accordingly, this invention addresses the above discussed problems and improves the bispecific antibody technology.

I. Conjugates

In one aspect of the invention, compounds of formula (Ia) are provided:

Wherein P is a non-immunogenic polymer; T is a multi-functional moiety, such as a trifunctional small molecule linker moiety, two of its functional groups are capable of site-specific conjugation with two different proteins. A1 and A2 are any two different proteins, such as antibody fragments or single chain antibodies or other forms of antibodies or any combination of such.

In particular, an aspect of the invention provides a conjugate of Formula Ib:

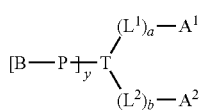

Formula Ib wherein:

P is a non-immunogenic polymer;

B is H, a terminal capping group or void, said capping group selected from $C_{1-50}$ alkyl and aryl, wherein one or more carbons of said alkyl may be replaced with a heteroatom;

T is a multi-functional linker, wherein the linkage between T and $(L^1)_a$ and the linkage between T and $(L^2)_b$ could be same or different;

each of $L^1$ and $L^2$ are independently a bifunctional linker;

a and b are each an integer selected from 0-10;

$A^1$ and $A^2$ are the same or different from each other and each of $A^1$ and $A^2$ independently comprises an antibody fragment, single chain antibody, or any other form of antibody or multispecific antibody or combination thereof; and y is an integer selected from 1-10.

The P moiety of the conjugate may be prepared from various non-imunogenic polymers. Preferably, the polymer is water-soluble. Examples of the polymers include dextrans, carbohydrate-based polymers, polyalkylene oxide, polyvinyl alcohols and other similar non-immunogenic polymers. Further exemplary polymers include poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), poly(vinyl alcohol), polyphosphazene, polyoxazoline, poly(N-acryloylmorpholine), or copolymers or terpolymers thereof. The polymers can be liner or branched. The average molecular weight of the polymer ranges from about 100 to about 100,000 daltons, such as about 3,000 to about 100,000 daltons, all subranges included.

The polymer may comprise a terminus group capable of being functionalized, activated, or conjugated to a reaction partner. Non-limiting examples of the terminus groups include hydroxyl, amino, carboxyl, thiol, and halide. In some embodiments, the polymer is polyethylene glycol (PEG).

In some embodiments, y is 1 and Formula Ib represents a conjugate with a pendent polymer chain. The terminal B may serve as a capping group.

In some embodiments, y is 2, 3, 4, 5 or 6 and Formula Ib represents a conjugate comprising a branched polymer moiety. In some embodiments, Bs in $[B-P]_y$ is a low molecular weight $C_{1-10}$ alkyl group such as methyl, ethyl, and butyl, wherein one or more of the carbons may be replaced by a heteroatom (e.g. O, S, and N).

Polymer Moiety P

In some embodiments, P represents a PEG moiety. In some embodiments, methods of preparing terminal branched heterobifunctional PEG that is capable of site-specific conjugating with two different proteins, such as antibody fragments or single chain antibodies, are provided. In some embodiments, methods for preparing PEGylated bispecific single chain antibody thereof that is able to extend blood circulation half life are also provided.

In exemplary embodiments, a terminal functional group of PEG such as hydroxyl or carboxyl group etc., is activated and conjugated with a trifunctional small molecule moiety such as Boc protected lysine to form a terminal branched heterobifunctional PEG. The newly formed carboxyl group is then converted to alkyne group by coupling with a small molecule spacer that has alkyne group. The naked amino group after Boc deprotection is conjugated with another small molecule spacer that has maleimide group to form a terminal branched maleimide/alkyne heterobifunctional PEG. The resulting maleimide/alkyne terminal branched heterobifunctional PEG is site-specifically conjugated with a thiol tagged single chain antibody and an azide tagged single chain antibody consecutively to form a PEGylated single chain bispecific antibody, which provides longer blood circulation half-life than none PEGylated single chain bispecific antibody.

PEGylated bispecific antibody of the formula (Ia) or (Ib) can be made by methods which includes by converting a PEG terminal functional group, such as hydroxyl, carboxyl group etc., into terminal branched heterobifunctional groups to form terminal branched heterobifunctional PEG such as terminal branched maleimide/alkyne heterobifunctional PEG. In some embodiments of present invention, the P moiety can be derived from a PEG of the formula:

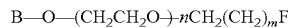

wherein:

n is an integer from about 10 to 2300 to preferably provide polymer having a total molecule weight of from 10000 to 40000 or greater if desired. B is methyl or other low molecule weight alkyl group or $-CH_2(CH_2)_mF$. Non-limiting examples of B include methyl, ethyl, isopropyl, propyl, and butyl. M is from 0 to 10. F is a terminal functional group such as hydroxyl, carboxyl, thiol, halide, amino group etc. which is capable of being functionalized, activated and/or conjugating a trifunctional small molecule compound.

In another embodiment of present invention, the method can also be carried out with an alternative branched PEG. The branched P moiety can be derived from a compound of the formula:

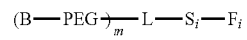

wherein:
PEG is polyethylene glycol. m is an integer greater than 1 to preferably provide polymer having a total molecule weight of from 10000 to 40000 or greater if desired. B is methyl or other low molecule weight alkyl group. L is a functional linkage moiety to that two or more PEGs are attached. Examples of such linkage moiety are: any amino acids such as glycine, alanine, Lysine, or 1,3-diamino-2-propanol, triethanolamine, any 5 or 6 member aromatic ring or aliphatic rings with more than two functional groups attached, etc. S is any non-cleavable spacer. F is a terminal functional group such as hydroxyl, carboxyl, thiol, amino group, etc. i is 0 or 1. When i equals to 0, the formula become:

wherein: the definitions of PEG, m, B or L have the same foregoing meaning.

In a related aspect, there is provided a conjugate with a multi-arm polymer moiety having the following Formula:

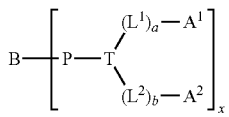

Wherein B serves as a core linking to 2, 3, 4, 5, 6, 7 or 8 polymer arms. The structure of core B can be symmetric or asymmetric, linear or cyclic. In some embodiments, B is a saturated aliphatic group. One or more carbons of the core may be replaced with a heteroatoms such as oxygen, sulfur or nitrogen. Core B, when taken together with the polymer arms, may be a residue of a polyol, polythiol or polyamine. Examples include, but are not limited to glycerol, trimethylol-propane, pentaerythritol, sorbitol, and oligomer of glycerol.

In some embodiments of the present invention, the multi-arm polymer moiety can be derived from a structure of the following formula.

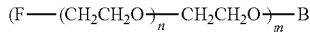

wherein:
n is an integer and from about 10 to 1200 and m is an integer and greater than 1 to preferably provide polymer having a total molecule weight of from 10000 to 40000 or greater if desired. F is a terminal functional group such as hydroxyl, carboxyl, thiol, amino group, etc. B is a non-functional linkage moiety to that two or more PEGs are attached. The structure of B can be symmetric or asymmetric, linear or cyclic saturated aliphatic group, and one or more carbons of B may be replaced with a heteroatoms such as oxygen, sulfur or nitrogen.

The method of the present invention can also be carried out with alternative polymeric substances such as dextrans, carbohydrate—base polymers, polyalkylene oxide, polyvinyl alcohols or other similar non-immunogenic polymers, the terminal groups of which are capable of being functionalized or activated to be converted to heterobifunctional groups. The foregoing list is merely illustrative and not intended to restrict the type of non-antigenic polymer suitable for use herein.

Trifunctional Linker T

T represents a trifunctional linker, connecting with P, $(L^1)_a$ and $(L^2)_b$. T can be derived from molecules with any combination of three functional groups, non-limiting examples of which include hydroxyl, amino, hydrazinyl, carboxyl, thiol, and halide. The functional groups may be the same or different in a trifunctional linker. In some embodiments, one or two of the functional groups may be protected to achieve selection conjugation with other reaction partners. A variety of protecting groups are known in the literature, including for example, Advanced Organic Chemistry by March (Third Edition, 1985, Wiley and Sons, New York). A functional group may also be converted into other groups before or after the reaction between T and another reaction partner. For example, a hydroxyl group may be converted into a mesylate or a tosylate group. A halide may be displaced with an azido group. An acid functional group of T may be converted to an alkyne function group by coupling with an amino group bearing a terminal alkyne.

In exemplary embodiments, T is derived from lysine, 1,3-diamino-2-propanol, or triethanolamine. One or more of the functional groups on these molecules may be protected for selective reactions. In some embodiments, T is derived from a BOC-protected lysine.

Bifunctional Linker $L^1$ and $L^2$

Both linker $L^1$ and $L^2$ comprises linker chains, internal linkages and/or terminal linkages. Linker chains and/or linkages (internal or terminal) may be independently selected from $-(CH_2)_aC(O)NR^1(CH_2)_b-$, $-(CH_2)_aO(CH_2CH_2O)_c-$, $-(CH_2)_a\text{heterocyclyl-}$, $-(CH_2)_aC(O)-$, and $-(CH_2)_aNR^1-$, $-CR^1=N-NR^1-$, $-CR^1=N-O-$, $-CR^1=N-NR^2-CO-$, $-N=N-CO-$, $-S-S-$, wherein a, b, and c are each an integer selected from 0 to 25, all subunits included; and $R^1$ and $R^2$ independently represent hydrogen or a C1-C10 alkyl.

Heterocyclyl linkage group within linker $L^1$ and $L^2$ (whether it is at internal position or at terminal position) may be derived from a maleimido-based moiety. Non-limiting examples of suitable precursors include N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester(MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI).

In some other non-limiting exemplary embodiments, each linker unit can also be derived from a haloacetyl-based moiety selected from N-succinimidyl-4-(iodoacetyl)-aminobenzoate (SIAB), N-succinimidyl iodoacetate (SIA), N-succinimidyl bromoacetate (SBA), or N-succinimidyl 3-(bromoacetamido)propionate (SBAP).

Alternatively, the heterocyclyl linkage group of the linker may be tetrazolyl or triazolyl which are formed from conjugations of different linker moieties. Thus, the heterocyclyl group also serve as a linkage point.

In some embodiments, each of $(L^1)_a$ and $(L^2)_b$ comprises:
$X^1-(CH_2)_aC(O)NR^1(CH_2)_bO(CH_2CH_2O)_c(CH_2)_dC(O)-$ or

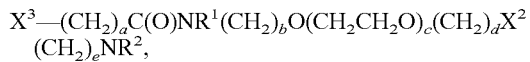
(CH$_2$)$_e$NR$^2$, wherein X$^1$, X$^2$ and X$^3$ may be the same or different and independently represent a heterocyclyl group;

a, b, c, d and e are each an integer selected from 1-25; and R$^1$ and R$^2$ independently represent hydrogen or a C1-C10 alkyl.

In some embodiments, X$^1$ and/or X$^3$ is derived from a maleimido-based moiety. In some embodiments, X$^2$ represents a triazolyl or a tetrazolyl group. In some embodiments, R$^1$ and R$^2$ each represent a hydrogen. In some embodiments, a, b, c, d and e are each independently selected from 0, 1, 2, 3, 4, 5, 6, 7, 8, 9, and 10.

Linkage Group

Different moieties of the conjugates of the present invention can be connected via various chemical linkages. Examples include but are not limited to amide, ester, disulfide, ether, amino, carbamate, hydrazine, thioether, and carbonate. For instance, the terminal hydroxyl group of a PEG moiety (P) may be activated and then coupled with lysine (T) to provide a desirable linkage point between P and T of Formula Ia or Ib. Meanwhile, the linkage group between T and L$^1$ or L$^2$ may be an amide resulting from the reaction between the amino group of a linker L$^1$ or L$^2$ and the carboxyl group of Lysine (T). Depending on the desirable characteristics of the conjugate, suitable linkage groups may also be incorporated between the antibody moiety (A) and the adjacent linker (L$^1$ or L$^2$) and between or within individual linkers of L$^1$ or L$^2$.

In some embodiments, the linkage group between different moieties of the conjugates may be derived from coupling of a pair of functional groups which bear inherent chemical affinity or selectivity for each other. These types of coupling or ring formation allow for site-specific conjugation for the introduction of a particular protein or antibody moiety. Non-limiting examples of these functional groups that lead to site-specific conjugation include thiol, maleimide, 2'-pyridyldithio variant, aromatic or vinyl sulfone, acrylate, bromo or iodo acetamide, azide, alkyne, dibenzocyclooctyl (DBCO), carbonyl, 2-amino-benzaldehyde or 2-amino-acetophenone group, hydrazide, oxime, potassium acyltrifluoroborate, O-carbamoylhydroxylamine, trans-cyclooctene, tetrazine, and triarylphosphine.

Synthesis

Key steps of the synthesis can be illustrated by the following embodiments. Once the desired PEG has been selected, the terminal functional group of PEG such as hydroxyl, carboxyl group etc. is converted to terminal branched heterobifunctional groups using any art-recognized process. Broadly stated, the terminal branched heterobifunctional PEG such as terminal branched heterobifunctional maleimide/alkyne PEG is prepared by activating terminal hydroxyl or carboxyl group of the PEG with N-Hydroxysuccinimide using reagents such as Di(N-succinimidyl) carbonate (DSC), triphosgene etc. in the case of terminal hydroxyl group or coupling reagents such as N,N'-Diisopropylcarbodiimide (DIPC), 1-Ethyl-3-(3-dimethylaminopropyl)carbodiimide (EDC) etc. in the case of terminal carboxyl group in the presence of base such as 4-Dimethylaminopyridine (DMAP), pyridine etc. to form activated PEG.

Next, the activated PEG is reacted with a trifunctional small molecule such as lysine derivative H-Lys(Boc)-OH in the presence of base such as Diisopropylamine (DIPE) to form a terminal branched heterobifunctional PEG with a free carboxyl group and a Boc protected amino group. As will be appreciated by those of ordinary skill, other known terminal functional groups of PEG such as halide, amino, thiol group etc and other known tri-functional small molecules can be used as alternatives for the same purpose if desired. Examples of tri-functional small molecules include the molecules containing any combination of three functional groups (NH2, NHNH2, COOH, OH, C═OX, N═C═X, S, anhydride, halides, maleimid, C═C, C≡C etc.) or their protected version.

The terminal branched carboxyl/Boc amino heterobifunctional PEG is then converted to a terminal branched alkyne/Boc amino heterobifunctional PEG by coupling with a small molecule spacer that has an alkyne group such as 1-amino-3-butyne or NH2-DBCO. Treatment of a terminal branched alkyne/Boc amino heterobifunctional PEG with an acid such as trifluoroacetic acid (TFA) gives the terminal branched alkyne/amine heterobifunctional PEG. The target terminal branched alkyne/maleimide heterobifunctional PEG is obtained by reacting the terminal branched alkyne/amine heterobifunctional PEG with another small molecule spacer that has a maleimide group such as NHS-PEG2-Maleimide. This terminal branched alkyne/maleimide heterobifunctional PEG is capable of site-specific conjugation with a thiol tagged antibody and a azide tagged antibody consecutively.

Separately, two single chain antibody (SCA) fragments, anti-CD3 (SCACD3) and anti-CD19 (SCACD19) can be generated using various technology known in the art. In one example, they are made via recombinant DNA technology in *Pichia pastorius* using an EasySelect™ Pichia Expression Kit containing a pPICZ vector. Genes of antibody such as anti-CD3 VH-VL and anti-CD19 VL-VH are synthesized and cloned into pPIZA expression vectors and transformed in a *P. pastoris* X33 strain. Expression of SCAs is induced by methanol and purified by Ni-chelating resin. To facilitate the subsequent conjugation, a site specific functional group such as thiol is inserted through recombinant DNA technology into the linker between VH and VL (Yang, K. et al. 2003, Protein Eng 16 (10): 761-770) of the single chain antibodies. Pure SCA is obtained via chromatographic process. As will be appreciated by those of ordinary skill, other known site specific functional groups can also be inserted through recombinant DNA technology into the linker between VH and VL of the SCA as alternatives for the same purpose if desired.

To prepare PEGylated single chain bispecific antibody, the terminal branched alkyne/maleimide heterobifunctional PEG is reacted site specifically with free thiol functional group of SCACD3 that is genetically inserted, resulting in PEG-(SCACD3)-alkyne, while SCACD19 is conjugated site specifically with a small molecule azide/maleimide bifunctional linker, resulting in azide-SCACD19. Purified azide-SCADCD19 and purified PEG-(SCACD3)-alkyne are reacted site specifically through an azide-alkyne clicking chemistry to form a target PEGylated single chain bispecific antibody PEG-SCACD3/SCACD19.

In addition to thiol/maleimide and azide/alkyne site specific conjugation group pair used in this invention, as will be appreciated by those of ordinary skill, other known pairs of site-specific conjugation groups, such as thiol/2'-pyridyldithio pair; thiol/sulfone pair; DBCO/azide pair; trans-cyclooctenes/tetrazines pair; carbonyl/hydrazide pair; carbonyl/oxime pair; azide/triarylphosphine pair; potassium acyltrifluoroborates/O-carbamoylhydroxylamines pair, can be similarly designed and used as alternatives for the same purpose if desired. The foregoing list of site-specific conjugation group pairs is merely illustrative and not intended to restrict the type of site-specific conjugation group pairs suitable for use herein.

Definitions of Terms

The term "alkyl" as used herein refers to a hydrocarbon chain, typically ranging from about 1 to 25 atoms in length. Such hydrocarbon chains are preferably but not necessarily saturated and may be branched or straight chain, although typically straight chain is preferred. The term C1-10 alkyl includes alkyl groups with 1, 2, 3, 4, 5, 6, 7, 8, 9 and 10 carbons. Similarly C1-25 alkyl includes all alkyls with 1 to 25 carbons. Exemplary alkyl groups include methyl, ethyl, isopropyl, n-butyl, n-pentyl, 2-methyl-1-butyl, 3-pentyl, 3-methyl-3-pentyl, and the like. As used herein, "alkyl" includes cycloalkyl when three or more carbon atoms are referenced. Unless otherwise noted, an alkyl can be substituted or un-substituted.

The term "functional group" as used herein refers to a group that may be used, under normal conditions of organic synthesis, to form a covalent linkage between the entity to which it is attached and another entity, which typically bears a further functional group. A "bifuncational linker" refers to a linker with two functional groups forms two linkages via with other moieties of a conjugate.

The term "derivative" as used herein refers to a chemically-modified compound with an additional structural moiety for the purpose of introducing new functional group or tuning the properties of the original compound.

The term "protecting group" as used herein refers to a moiety that prevents or blocks reaction of a particular chemically reactive functional group in a molecule under certain reaction conditions. Various protecting groups are well-known in the art and are described, for example, in T. W. Greene and G. M. Wuts, Protecting Groups in Organic Synthesis, Third Edition, Wiley, New York, 1999, and in P. J. Kocienski, Protecting Groups, Third Ed., Thieme Chemistry, 2003, and references cited therein.

The term "PEG" or "poly(ethylene glycol)" as used herein refers to poly(ethylene oxide). PEGs for use in the present invention typically comprise a structure of —(CH2CH2O)n—. PEGs may have a variety of molecular weights, structures or geometries. A PEG group may comprise a capping group that does not readily undergo chemical transformation under typical synthetic reaction conditions. Examples of capping groups include —OC1-25 alkyl or —OAryl.

The term "linker" as used herein refers to an atom or a collection of atoms used to link interconnecting moieties, such as an antibody and a polymer moiety. A linker can be cleavable or noncleavable. The preparation of various linkers for conjugates have been described in literatures including for example Goldmacher et al., Antibody-drug Conjugates and Immunotoxins: From Pre-clinical Development to Therapeutic Applications, Chapter 7, in Linker Technology and Impact of Linker Design on ADC properties, Edited by Phillips G L; Ed. Springer Science and Business Media, New York (2013). Cleavable linkers incorporate groups or moieties that can be cleaved under certain biological or chemical conditions. Examples include enzymatically cleavable disulfide linkers, 1,4- or 1,6-benzyl elimination, trimethyl lock system, bicine-based self cleavable system, acid-labile silyl ether linkers and other photo-labile linkers.

The term "linking group" or "linkage group" as used herein refers to a functional group or moiety connecting different moieties of a compound or conjugate. Examples of a linking group include, but are not limited to, amide, ester, carbamate, ether, thioether, disulfide, hydrazone, oxime, and semicarbazide, carbodiimide, acid labile group, photolabile group, peptidase labile group and esterase labile group. For example, a linker moiety and a polymer moiety may be connected to each other via an amide or carbamate linkage group.

The term "multiple arms" or "multi-armed" as used herein refers to the geometry or overall structure of a polymer refers to polymer having 2 or more polymer-containing "arms" connected to a "core" molecule or structure. Thus, a multi-armed polymer may possess 2, 3, 4, 5, 6, 7, 8 arms or more.

II. Multi-Specific Molecules and Antibodies

The present invention encompasses multi-specific molecules having two or more different recognition specificities. The multi-specific molecules of the invention refer to molecules comprising among others a first recognition binding moiety that binds a first target and a second recognition binding moiety that binds to a second target. In a specific embodiment, one or both of the recognition binding moieties are antibodies or the antigen binding portions thereof.

Antibodies

The multi-specific molecules of the present invention can be made using any isolated antibodies, in particular monoclonal antibodies such as human monoclonal antibodies that bind to different antigens or epitopes. Preferably the antibodies are human antibodies, although the antibodies can also be, for example, murine antibodies, chimeric antibodies, humanized antibodies, or a combination thereof.

Structure Components

Monoclonal antibody techniques allow for the production of specifically binding agents in the form of specifically binding monoclonal antibodies or fragments thereof. For creating monoclonal antibodies, or fragments thereof, one can use conventional hybridoma techniques. Alternatively monoclonal antibodies, or fragments thereof, can be obtained by the use of phage libraries of scFv (single chain variable region), specifically human scFv (see e.g. U.S. Pat. No. 5,885,793, WO 92/01047, WO 99/06587).

In one embodiment, at least one of the recognition binding moieties in the multi-specific molecule of the present invention is a monovalent antibody fragment. In one embodiment the monovalent antibody fragment is derived from a monoclonal antibody. Monovalent antibody fragments include, but are not limited to Fab, Fab'-SH, single domain antibody, F(ab')$_2$, Fv, and scFv fragments. Thus, in one embodiment the monovalent antibody fragment is selected from the group comprising Fab, Fab'-SH, single domain antibody, F(ab')$_2$, Fv, and scFv fragments. In one embodiment at least one of the recognition binding moieties of the multi-specific molecules disclosed herein is a single domain antibody, or scFv or a Fab-fragment, or a Fab'-fragment of a monoclonal antibody.

One or more of the recognition binding moiety in the multi-specific molecules can also be diabodies or single-domain antibodies. Diabodies are antibody fragments with two antigen-binding sites that may be bivalent or bispecific (see e.g. EP 0 404 097, WO 93/01161, Hudson, P. J., et al., Nat. Med. 9 (2003) 129-134, and Holliger, P., et al., Proc. Natl. Acad. Sci. USA 90 (1993) 6444-6448). Triabodies and tetrabodies as described in Hudson, P. J., et al., Nat. Med. 9 (2003) 129-134 can also be used for a recognition binding moiety in the multi-specific molecules. Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; U.S. Pat. No. 6,248,516).

A recognition binding moiety in the multi-specific molecules can be an Fv, which is a minimum antibody fragment that contains a complete antigen-binding site and is devoid of constant region. For a review of scFv, see, e.g., Plueckthun, in The Pharmacology of Monoclonal Antibodies, vol. 113, Rosenburg and Moore (eds.), (Springer-Verlag, New York, 1994), pp. 269-315, WO 93/16185, U.S. Pat. Nos. 5,571,894, 5,587,458. Generally, six hyper variable regions (HVRs) confer antigen-binding specificity to an antibody. However, even a single variable domain (or half of an Fv comprising only three HVRs specific for an antigen) has the ability to recognize and bind its antigen.

In one embodiment the monovalent antibody fragments is a two-chain Fv species consisting of a dimer of one heavy- and one light-chain variable domain in tight, non-covalent association. In one embodiment the monovalent antibody fragments is a single-chain Fv (scFv) species consisting of one heavy-chain and one light-chain variable domain covalently linked by a flexible peptide linker.

A Fab fragment of an antibody contains the heavy-chain and light-chain variable domains as well as the constant domain of the light chain and the first constant domain (CH1) of the heavy chain. A Fab' fragments differ from a Fab fragment by the addition of a few residues at the carboxy terminus of the heavy chain CH1 domain including one or more cysteines from the antibody hinge region. Fab'-SH denotes a Fab' in which the cysteine residue(s) of the constant domains bear a free thiol group.

Various techniques have been developed for the production of antibody fragments. Traditionally, antibody fragments can be obtained via proteolytic digestion of full length antibodies (see, e.g., Morimoto, K., et al., J. Biochem. Biophys. Meth. 24 (1992) 107-117, Brennan, M., et al., Science 229 (1985) 81-83). For example, papain digestion of full length antibodies results in two identical antigen-binding fragments, called "Fab" fragments, each with a single antigen-binding site, and a residual "Fc" fragment. For a review of certain antibody fragments, see Hudson, P. J., et al., Nat. Med. 9 (2003) 129-134.

Antibody fragments can also be produced directly by recombinant means. Fab, Fv and scFv antibody fragments can all be expressed in and secreted from e.g. *E. coli*, thus, allowing the facile production of large amounts of these fragments. Antibody fragments can be isolated from antibody phage libraries according to standard procedures. Alternatively, Fab'-SH fragments can be directly recovered from *E. coli*. (Carter, P., et al., Bio/Technology 10 (1992) 163-167). Mammalian cell systems can be also used to express and, if desired, secrete antibody fragments.

Targets

A number of therapeutic antibodies directed against cell surface molecules and/or their ligands are known. These antibodies can be used for the selection and construction of tailor-made specific recognition binding moiety in the multi-specific molecules. Examples include Blinatumomab/BLIN-CYTO Rituxan/MabThera/Rituximab, H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAMS/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

The multispecific binding molecules/multi-specific antibodies disclosed herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha-fetoprotein, alpha-ctinin-4, A3 (antigen specific for A33 antibody), ART-4, B7-1, B7-H1, Ba-733, BAGE, BrE3-antigen, CA125, CAMEL, CAP-1, CASP-8/m, CCCL19, CCCL21, CD1, CD1a, CD2, CD3, CD4, CD S, CD8, CD1-1A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD137, CD138, CD147, CD154, CDC27, CDK-4/m, CDKN2A, CTLA-4, CXCR4, CXCR7, CXCL12, HIF-1-α, colon-specific antigen-p (CSAp), CEA (CEACAMS), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-γ, IFN-α, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS 1-4, LAG3, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, PD-1 and its receptor, PD-L1, PD-L2, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TIM3(T-cell immunoglobulin and mucin-domain containing-3), TRAIL receptors, TNF-α, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin. Cancer Res. 12 (2006) 5023-5032; Parmiani et al, J. Immunol. 178 (2007) 1975-1979; Novellino et al., Cancer Immunol. Immunother. 54 (2005) 187-207). Thus, antibodies recognizing such specific cell surface receptors or their ligands can be used for specific and selective recognition binding moieties in the multi-specific molecules of this invention, targeting and binding to a number/multitude of cell surface markers or ligands that are associated with a disease.

In some embodiments, for the treatment of cancer/tumors multispecific binding molecules/multi-specific antibodies are used that target tumor-associated antigens (TAAs), such as those reported in Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744.

Reports on tumor associated antigens include Mizukami et al., Nature Med. 11 (2005) 992-997; Hatfield et al., Curr. Cancer Drug Targets 5 (2005) 229-248; Vallbohmer et al., J. Clin. Oncol. 23 (2005) 3536-3544; and Ren et al., Ann. Surg. 242 (2005) 55-63), each incorporated herein by reference with respect to the TAAs identified. Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

Antibodies against the above-mentioned antigens can be used as the binding sites or moieties to make bispecific antibodies of this invention. A number of bispecific antibodies can be made against two different targets.

Examples of the antigen pairs include CD19/CD3, BCMA/CD3, different antigens of the HER family in combination (EGFR, HER2, HER3), IL17RA/IL7R, IL-6/IL-23, IL-1-β/IL-8, IL-6 or IL-6R/IL-21 or IL-21R, ANG2/VEGF, VEGF/PDGFR-beta, Vascular Endothelial Growth Factor (VEGF) acceptor 2/CD3, PSMA/CD3, EPCAM/CD3, combinations of antigens selected from a group consisting of VEGFR-1, VEGFR-2, VEGFR-3, FLT3, c-FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PIGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16. Additional examples of bispecific antibodies can have (i) a first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, and sialyltetraosylceramide and (ii) a second specificity directed to an ErbB receptor tyrosine kinase selected from the group consisting of EGFR, HER2, HER3 and HER4. GD2 in combination with a second antigen binding site is associated with an immunological cell chosen from the group consisting of T-lymphocytes NK cell, B-lymphocytes, dendritic cells, monocytes, macrophages, neutrophils, mesenchymal stem cells, neural stem cells.

A monospecific or bispecific antibody can be joined together with another monospecific or bispecific antibody using the method disclosed herein to make multi-specific antibodies. By using already available monospecific or bispecific therapeutic binding entities, such as those therapeutic antibodies described above, a fast and easy production of the required multispecific binding molecule can be achieved. With this tailor-made generation of multispecific therapeutics by combining two or more single therapeutic molecules for simultaneous targeting and binding to two or more different epitopes, an additive/synergistic effect can be expected in comparison to the single therapeutic molecules.

In some embodiments, multi-specific molecules of this invention are made using antibody pairs that specifically interact and show measurable affinities to the following target pairs.

| Single chain antibody fragments Targets | Mechanisms of action | Diseases (or healthy volunteers) |
| --- | --- | --- |
| CD3, EpCAM | Retargeting of T cells to tumor<comma> Fc mediated effector functions | Malignant ascites in EpCAM positive tumors |
| CD3, HER2 | Retargeting of T cells to tumor | Advanced solid tumors |
| CD3, CD19 | Retargeting of T cells to tumor | Precursor B-cell ALLALLDLBCLNHL |
| CD3, EpCAM | Retargeting of T cells to tumor | Solid tumors |
| CD3, CEA | Retargeting of T cells to tumor | Gastrointestinal adenocarcinoma |
| CD3, PSMA | Retargeting of T cells to tumor | Prostate cancer |
| CD3, CD123 | Retargeting of T cells to tumor | AML |
| CD3, gpA33 | Retargeting of T cells to tumor | Colorectal cancer |
| CD3, CD19 | Retargeting of T cells to tumor | NHL and ALL |
| CD30, CD16A | Retargeting of NK cells to tumor cells | Hodgkin's Lymphoma |
| CD3, GD2 | Retargeting of T cells to tumor | Neuroblastoma and osteosarcoma |

| Single chain antibody fragments Targets | Mechanisms of action | Diseases (or healthy volunteers) |
|---|---|---|
| CD3, Her2 | Retargeting of T cells to tumor | Metastatic breast cancer |
| CD3, EGFR | Autologous activated T cells to EGFR-positive tumor | Lung and other solid tumors |
| CD3, EGFR | Autologous activated T cells to EGFR-positive tumor | Colon and pancreatic cancers |
| CD3, PD-L1 | Retargeting of T cells to tumor | solid tumors |
| CD28, MAPG | Retargeting of T cells to tumor | Metastatic melanoma |
| CD3, peptide MHC | Retargeting of T cells to tumor | Metastatic melanoma |
| CD19, CD22 | Targeting of protein toxin to tumor | B cell leukemia or lymphoma |
| EGFR, HER3 | Blockade of 2 receptors, ADCC | Head and neck cancer<br>Colorectal cancer |
| EGFR, MET | Blockade of 2 receptors | Advanced or metastatic cancer |
| HER2, HER3 | Blockade of 2 receptors | Gastric and esophageal cancers<br>Breast cancer |
| IGF-1R, HER3 | Blockade of 2 receptors | Advanced solid tumors |
| Ang2, VEGF A | Blockade of 2 proangiogenics | Solid tumors |
| Ang2, VEGF A | Blockade of 2 proangiogenics | Wet AMD |
| CEA, HSG | Pretargeting tumor for PET or radioimaging | Colorectal<comma> breast and lung cancers |
| IL-1α, IL-1β | Blockade of 2 proinflammatory cytokines | Osteoarthritis |
| TNF, IL-17A | Blockade of 2 proinflammatory cytokines | Rheumatoid arthritis |
| TNF, IL17A | Blockade of 2 proinflammatory cytokines | Plaque psoriasis |
| IL-13, IL-4 | Blockade of 2 proinflammatory cytokines | Idiopathic pulmonary fibrosis |
| IL-13, IL-4 | Blockade of 2 proinflammatory cytokines | (Healthy volunteers) |
| TNF, HSA | Blockade of proinflammatory cytokine, binds to HSA to increase half-life | Rheumatoid arthritis |
| IL-17A/F, HSA | Blockade of 2 proinflammatory cytokines, binds to HSA to increase half-life | (Healthy volunteers) |
| IL-6R, HSA | Blockade of proinflammatory cytokine, binds to HSA to increase half-life | Rheumatoid arthritis |
| RANKL, HSA | Blockade of bone resorption, binds to HSA to increase half-life | Postmenopausal bone loss |
| Factor Ixa, factor X | Plasma coagulation | Hemophilia |

In a preferred embodiment, a bispecific molecule is a conjugate of two antibodies or antigen-binding fragments thereof that specifically interact and show measurable affinities to CD3 and CD19, respectively. Each of the antibody binds to human CD3 or CD19 with a $K_D$ of $1\times10^{-6}$ M or less, e.g., $1\times10^{-7}$ M, $5\times10^{-8}$ M, $1\times10^{-8}$ M, $5\times10^{-9}$ M, $1\times10^{-9}$ M or less, or $K_D$ of between $1\times10^{-8}$ M and $1\times10^{-10}$ M. Assays to evaluate the binding ability of the antibodies toward antigens are known in the art, including for example, ELISAs, Western blots and RIAs. The binding kinetics (e.g., binding affinity) of the antibodies also can be assessed by standard assays known in the art, such as by Biacore analysis.

In certain embodiments, the first or second recognition binding moiety comprises the heavy chain and light chain, or corresponding CDR1s, CDR2s and CDR3s of antibodies of interest. For example, each recognition binding moiety can be a single chain antibody Fv region (scFv). The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Listed below are amino acid sequences of anti-CD3 scFv and anti-CD19 scFv.

Anti-CD3 scFv sequence (SEQ ID No: 1):
Asp Ile Lys Leu Gln Gln Ser Gly Ala Glu Leu Ala Arg Pro Gly Ala Ser Val Lys Met Ser Cys Lys Thr Ser Gly Tyr Thr Phe Thr Arg Tyr Thr Met His Trp Val Lys Gln Arg Pro Gly Gln Gly Leu Glu Trp Ile Gly Tyr Ile Asn Pro Ser Arg Gly Tyr Thr Asn Tyr Asn Gln Lys Phe Lys Asp Lys Ala Thr Leu Thr Thr Asp Lys Ser Ser Ser Thr Ala Tyr Met Gln Leu Ser Ser Leu Thr Ser Glu Asp Ser Ala Val Tyr Tyr Cys Ala Arg Tyr Tyr Asp Asp His Tyr Cys Leu Asp Tyr Trp Gly Gln Gly Thr Thr Leu Thr Val Ser Ser Val Glu Gly Cys Gly Ser Gly Gly Ser Gly Gly Ser Gly Gly Ser Gly Gly Val Asp Asp Ile Gln Leu Thr Gln Ser Pro Ala Ile Met Ser Ala Ser Pro Gly Glu Lys Val Thr Met Thr Cys Arg Ala Ser Ser Ser Val Ser Tyr Met Asn Trp Tyr Gln Gln Lys Ser Gly Thr Ser Pro Lys Arg Trp Ile Tyr Asp Thr Ser Lys Val Ala Ser Gly Val Pro Tyr Arg Phe Ser Gly Ser Gly Ser Gly Thr Ser Tyr Ser Leu Thr Ile Ser Ser Met Glu Ala Glu Asp Ala Ala Thr Tyr Tyr Cys Gln Gln Trp Ser Ser Asn Pro Leu Thr Phe Gly Ala Gly Thr Lys Leu Glu Leu Lys -continued
Anti-CD19 scFv sequence (SEQ ID No: 2):
Asp Ile Gln Leu Thr Gln Ser Pro Ala Ser Leu Ala Val Ser Leu Gly Gln Arg Ala Thr Ile Ser Cys Lys Ala Ser Gln Ser Val Asp Tyr Asp Gly Asp Ser Tyr Leu Asn Trp Tyr Gln Gln Ile Pro Gly Gln Pro Pro Lys Leu Leu Ile Tyr Asp Ala Ser Asn Leu Val Ser Gly Ile Pro Pro Arg Phe Ser Gly Ser Gly Ser Gly Thr Asp Phe Thr Leu Asn Ile His Pro Val Glu Lys Val Asp Ala Ala Thr Tyr His Cys Gln Gln Ser Thr Glu Asp Pro Trp Thr Phe Gly Gly Gly Thr Lys Leu Glu Ile Lys Gly Cys Gly Gly Gly Ser Gly Gly Gly Gly Ser Gly Gly Gly Gly Ser Gln Val Gln Leu Gln Gln Ser Gly Ala Glu Leu Val Arg Pro Gly Ser Ser Val Lys Ile Ser Cys Lys Ala Ser Gly Tyr Ala Phe Ser Ser Tyr Trp Met Asn Trp Val Lys Gln Arg Pro Gly Gln Gly Leu Glu Trp Ile Gly Gln Ile Trp Pro Gly Asp Gly Asp Thr Asn Tyr Asn Gly Lys Phe Lys Gly Lys Ala Thr Leu Thr Ala Asp Glu Ser Ser Ser Thr Ala Tyr Met Gln Leu Ser Ser Leu Ala Ser Glu Asp Ser Ala Val Tyr Phe Cys Ala Arg Arg Glu Thr Thr Val Gly Arg Tyr Tyr Tyr Ala Met Asp Tyr Trp Gly Gln Gly Thr Thr Val Thr Val Ser Ser Modifications In some embodiments, the $V_H$ and/or $V_L$ amino acid sequences of the antibodies may be 82% 85%, 90%, 95%, 96%, 97%, 98% or 99% homologous to the sequences set forth above and retain the corresponding antigen-binding activity and specificity. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding the above-mentioned heavy chain and light chain, or related CDR1s, CDR2s and CDR3s, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

In certain embodiments, an recognition binding moiety of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties.

As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include:
  amino acids with basic side chains (e.g., lysine, arginine, histidine),
  acidic side chains (e.g., aspartic acid, glutamic acid),
  uncharged polar side chains (e.g., glycine, asparagine, glutamine, serine, threonine, tyrosine, cysteine, tryptophan),
  nonpolar side chains (e.g., alanine, valine, leucine, isoleucine, proline, phenylalanine, methionine),
  beta-branched side chains (e.g., threonine, valine, isoleucine) and
  aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function using the functional assays described herein.

A recognition binding moiety of the invention can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.).

Such framework sequences can be obtained from public DNA databases or published references that include germline antibody gene sequences. For example, germline DNA sequences for human heavy and light chain variable region genes can be found in the "VBase" human germline sequence database (available at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are incorporated herein by reference. As another example, the germline DNA sequences for human heavy and light chain variable region genes can be found in the GenBank database.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. The numbering of residues in the Fc region is that of the EU index of Kabat.

In still another embodiment, the glycosylation of an antibody can be modified. Glycosylation can be altered to, for example, increase or decrease the affinity of the antibody for antigen or an Fc receptor. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 8,008,449 and 6,350,861.

Effectors

In some embodiments, the multi-specific compound or molecule can be further conjugated to one or more effector moieties, e.g. cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, the effector moiety can be a drug, including but not limited to a maytansinoid (see U.S. Pat. Nos. 5,208,020, 5,416,064, EP 0 425 235), an auristatin such as monomethylauristatin drug moieties DE and DF (MMAE and MMAF, see U.S. Pat. Nos. 5,635,483, 5,780,588, 7,498, 298), a dolastatin, a calicheamicin or derivative thereof (see U.S. Pat. Nos. 5,712,374, 5,714,586, 5,739,116, 5,767,285, 5,770,701, 5,770,710, 5,773,001, 5,877,296, Hinman, L. M., et al., Cancer Res. 53 (1993) 3336-3342, Lode, H. N., et al., Cancer Res. 58 (1998) 2925-2928), an anthracycline such as daunomycin or doxorubicin (see Kratz, F., et al., Current Med. Chem. 13 (2006) 477-523, Jeffrey, S. C., et al., Bioorg. Med. Chem. Letters 16 (2006) 358-362, Torgov, M. Y., et al., Bioconjug. Chem. 16 (2005) 717-721, Nagy, A., et al., Proc. Natl. Acad. Sci. USA 97 (2000) 829-834, Dubowchik, G. M., et al., Bioorg. Med. Chem. Lett. 12 (2002) 1529-1532, King, H. D., et al., J. Med. Chem. 45 (2002) 4336-4343, and U.S. Pat. No. 6,630,579), methotrexate, vindesine, a taxane such as docetaxel, paclitaxel, larotaxel, tesetaxel, and ortataxel, a trichothecene, and CC1065.

In other embodiments, the effector moiety can be an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In yet some other embodiments, the effector moiety can be a radioactive atom. A variety of radioactive isotopes are available for the production of radioconjugates. Examples include $At^{211}$, $I^{131}$, $I^{125}$, $Y^{90}$, $Re^{186}$, $Re1^{88}$, $Sm1^{53}$, $Bi^{212}$, $P^{32}$, $Pb^{212}$, and radioactive isotopes of Lu. When the radioconjugate is used for detection, it may comprise a radioactive atom for scintigraphic studies, for example Tc99 or I123, or a spin label for nuclear magnetic resonance (NMR) imaging (also known as magnetic resonance imaging, MRI), such as $I^{123}$ again, $I^{131}$, $In^{111}$, $F^{19}$, $C^{13}$, $N^{15}$, $O^{17}$, gadolinium, manganese or iron.

The effector moiety can be conjugated to any component of the multi-specific compound or molecule disclosed herein using a variety of bifunctional protein coupling agents such as N-succinimidyl-3-(2-pyridyldithio) propionate (SPDP), succinimidyl-4-(N-maleiimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido components (such as bis(p-azidobenzoyl) hexane diamine), bis-diazonium derivatives (such as bis-(p-diazoniumbenzoyl)-ethylene diamine), diisocyanates (such as toluene 2,6-diisocyanate), and bis-active fluorine components (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine penta acetic acid (MX-DTPA) is an exemplary chelating agent for conjugation of radionucleotide to the complex (see WO 94/11026). The linker for conjugating the toxic moiety to the complex as reported herein can be a "cleavable linker" facilitating release of a cytotoxic drug in the cell. For example, an acid-labile linker, peptidase-sensitive linker, photolabile linker, dimethyl linker, or disulfide-containing linker (Chari, R. V., et al., Cancer Res. 52 (1992) 127-131, U.S. Pat. No. 5,208,020) can be used.

The effector moiety may be conjugated to a multi-specific compound or molecule disclosed herein, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Compositions

The present invention also provides a composition, e.g., a pharmaceutical composition, containing multi-specific molecules of the present invention, formulated together with a pharmaceutically acceptable carrier. For example, a pharmaceutical composition of the invention can comprise a multi-specific molecule that binds to both CD13 and CD9.

Therapeutic formulations of this invention can be prepared by mixing the multi-specific molecules having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS, or polyethylene glycol (PEG).

The formulation may also contain more than one active compound as necessary for the particular indication being treated, preferably those with complementary activities that do not adversely affect each other. For instance, the formulation may further comprise another antibody, cytotoxic agent, or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the multi-specific molecules, which matrices are in the form of shaped articles, e.g., films, or microcapsule. Examples of sustained-releasable matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical compositions of the invention can be administered in combination therapy, i.e., combined with other agents. Examples of therapeutic agents that can be used in combination therapy are described in greater detail below.

The formulations to be used for in vivo administration must be sterile. This can be readily accomplished by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the multi-specific molecules of this invention, the dosage ranges from about 0.0001 to 100 mg/kg, and more usually 0.01 to 50 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for multi-specific molecules of the invention include 1 mg/kg body weight or 3 mg/kg body weight via intravenous administration, with the multi-specific molecule being given using one of the following dosing schedules: (i) every four weeks for six dosages, then every three months; (ii) every three weeks; (iii) 3 mg/kg body weight once followed by 1 mg/kg body weight every three weeks.

Alternatively, multi-specific molecules can be administered as a sustained release formulation, in which case less frequent administration is required. Dosage and frequency vary depending on the half-life of the multi-specific molecules in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a multi-specific molecule of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth or metastasis by at least about 20%, more preferably by at least about 40%, even more preferably by at least about 60%, and still more preferably by at least about 80% relative to untreated subjects. The ability of an agent or compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, metastasis, or otherwise ameliorate symptoms in a subject. One of ordinary skill in the art would be able to determine such amounts based on such factors as the subject's size, the severity of the subject's symptoms, and the particular composition or route of administration selected.

Administration

A composition of the invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a multi-specific molecule of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, and 4,596,556. Examples of well-known implants and modules useful in the present invention include those described in U.S. Pat. Nos. 4,487,603, 4,486,194, 4,447,233, 4,447,224, 4,439,196, and 4,475,196. These patents are incorporated herein by reference. Many other such implants, delivery systems, and modules are known to those skilled in the art.

Treatment Methods

In one aspect, the present invention relates to treatment of a subject in vivo using the above-described multi-specific molecule such that growth and/or metastasis of cancerous tumors is inhibited. In one embodiment, the invention provides a method of inhibiting growth and/or restricting metastatic spread of tumor cells in a subject, comprising administering to the subject a therapeutically effective amount of a multi-specific molecule.

Non-limiting examples of preferred cancers for treatment include chronic or acute leukemia including acute myeloid leukemia, chronic myeloid leukemia, acute lymphoblastic leukemia, chronic lymphocytic leukemia, lymphocytic lymphoma, breast cancer, ovarian cancer, melanoma (e.g., metastatic malignant melanoma), renal cancer (e.g. clear cell carcinoma), prostate cancer (e.g. hormone refractory prostate adenocarcinoma), colon cancer and lung cancer (e.g. non-small cell lung cancer). Additionally, the invention includes refractory or recurrent malignancies whose growth may be inhibited using the antibodies of the invention. Examples of other cancers that may be treated using the methods of the invention include bone cancer, pancreatic cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

As used herein, the term "subject" is intended to include human and non-human animals. Non-human animals includes all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the immune response.

The above treatment may also be combined with standard cancer treatments. For example, it may be effectively combined with chemotherapeutic regimes. In these instances, it may be possible to reduce the dose of chemotherapeutic reagent administered (Mokyr, M. et al. (1998) Cancer Research 58: 5301-5304).

Other antibodies which may be used to activate host immune responsiveness can be used in combination with the multi-specific molecule of this invention. These include molecules targeting on the surface of dendritic cells which activate DC function and antigen presentation. For example, anti-CD40 antibodies are able to substitute effectively for T cell helper activity (Ridge, J. et al. (1998) Nature 393: 474-478) and can be used in conjunction with the multi-specific molecule of this invention (Ito, N. et al. (2000) Immunobiology 201 (5) 527-40). Similarly, antibodies targeting T cell costimulatory molecules such as CTLA-4 (e.g., U.S. Pat. No. 5,811,097), CD28 (Haan, J. et al. (2014) Immunology Letters 162:103-112), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) or antibodies targeting PD-1 (U.S. Pat. No. 8,008,449) PD-1L (U.S. Pat. Nos. 7,943,743 and 8,168,179) may also provide for increased levels of T cell activation. In another example, the multi-specific molecule of this invention can be used in conjunction with anti-neoplastic antibodies, such as RITUXAN (rituximab), HERCEPTIN (trastuzumab), BEXXAR (tositumomab), ZEVALIN (ibritumomab), CAMPATH (alemtuzumab), LYMPHOCIDE (eprtuzumab), AVASTIN (bevacizumab), and TARCEVA (erlotinib), and the like.

Definition of Terms

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

An "antigen" refers to a substance that elicits an immunological reaction or binds to the products of that reaction. The term "epitope" refers to the region of an antigen to which an antibody or T cell binds.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding and/or variable region of the intact antibody and/or the Fc region of an antibody which retains FcR binding capability. Examples of antibody fragments include linear antibodies; single-chain antibody molecules; and multispecific antibodies formed from antibody fragments. Preferably, the antibody fragments retain the entire constant region of an IgG heavy chain, and include an IgG light chain.

As used herein, the term "Fc fragment" or "Fc region" is used to define a C-terminal region of an immunoglobulin heavy chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., Nature, 352, 624-628 (1991) and Marks et al., J Mol Biol, 222, 581-597 (1991), for example, each of which is incorporated herein by reference.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., Proc Natl Acad Sci USA, 81, 6851-6855 (1984); Neuberger et al., Nature, 312, 604-608 (1984); Takeda et al., Nature, 314, 452-454 (1985); International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., Nature, 321, 522-525 (1986); Riechmann et al., Nature, 332, 323-329 (1988); Presta, Curr Op Struct Biol, 2, 593-596 (1992); U.S. Pat. No. 5,225,539, each of which is incorporated herein by reference.

"Human antibodies" refer to any antibody with fully human sequences, such as might be obtained from a human hybridoma, human phage display library or transgenic mouse expressing human antibody sequences.

The term "pharmaceutical composition" refers to the combination of an active agent with a carrier, inert or active, making the composition especially suitable for diagnostic or therapeutic use in vivo or ex vivo.

As used herein, "pharmaceutically acceptable carrier" includes any and all solvents, dispersion media, coatings, antibacterial and antifungal agents, isotonic and absorption delaying agents, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences. Preferably, the carrier is suitable for intravenous, intramuscular, subcutaneous, parenteral, spinal or epidermal administration (e.g., by injection or infusion). The therapeutic compounds may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As used herein, "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

An "effective amount" refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment. A therapeutically effective amount of a combination to treat a neoplastic condition is an amount that will cause, for example, a reduction in tumor size, a reduction in the number of tumor foci, or slow the growth of a tumor, as compared to untreated animals.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

EXAMPLES

Example 1. Preparation of 30 kmPEG-Lys(maleimide)-alkyne (FIG. 1A)

Preparation of 30 kmSC-PEG (Compound 2)

25 g of 30 kmPEG-OH (MW=30000, 1 eq) was azeotroped for two hours with 360 mL of reagent toluene to remove 75 mL toluene/water. After azeotroping, the solution was cooled to 45-50° C. 166 mg of triphosgene (0.67 eq.) was added to PEG followed by 131.8 mg of anhydrous pyridine (2 eq.). Reaction was stirred at 50° C. for 3 hours. 239.8 mg of N-hydroxysuccinimide (2.5 eq.) was then added followed by 164.8 g of anhydrous pyridine (2.5 eq.). The reaction mixture was stirred at 50° C. overnight under nitrogen. Pyridine salt was filtered. Solvent was removed with Rotavapor and the residue was recrystallized from 2-propanol. The isolated product was dried in vacuum oven at 40° C. to yield 23 g of 30 kmSC-PEG.

Preparation of 30 kmPEG-Lys(Boc)-OH
(Compound 3)

369 mg of H-lys(boc)-OH (3 eq.), 646.5 mg of DIEA (10 eq.) and 15 g of 30 kmSCPEG (1 eq.) were mixed in 100 mL DMF and 150 ml DCM. The mixture was stirred at room temperature overnight. The insoluble materials were filtered off. The solvent was removed and the residue was recrystallized from 2-propanol. The isolated product was dried at 40° C. under vacuum to yield 12.8 g of 30 kmPEG-Lys(Boc)-OH.

Preparation of 30 kmPEG-Lys(Boc)-alkyne
(Compound 4)

11 g of 30 kmPEG-Lys(Boc)-OH (1 eq.) was dissolved in 110 mL of DCM and cooled to 0-5° C. 101.4 mg of 1-amino-3-butyne (4 eq.) was added followed by 402.6 mg of DMAP (9 eq.) and 422.4 mg of EDC (6 eq). The mixture was stirred at 0-5° C. for 1 hour. The cooling was removed and the reaction was left at room temperature overnight. Solvent was removed and the residue was recrystallized from 2-propanol. The isolated product was dried under vacuum at 40° C. to yield 10.4 g of 30 kmPEG-Lys(Boc)-alkyne.

Preparation of 30 kmPEG-Lys-alkyne (Compound 5)

10 g of 30 kmPEG-lys(Boc)-alkyne is treated with 150 mL of TFA/DCM (1:2) at room temperature for 1 hr. Solvent is removed under vacuum. The residue is recrystallized from ethyl ether/DCM. The isolated product is dried under vacuum at 40° C. to yield 9.5 g of 30 kmPEG-Lys-alkyne.

Preparation of 30 kmPEG-Lys(maleimide)-alkyne
(Compound 6)

9 g of 30 kmPEG-lys-alkyne (1 eq.) was dissolved in 90 mL of DCM. 774 mg of DIEA (20 eq) was added followed by 281 mg of NHS-PEG2-Mal (2.2 eq) at 0/5° C. The mixture was stirred at room temperature overnight. Solvent was removed and the residue was recrystallized from 2-propanol. The isolated product was dried under vacuum to yield 8 g of 30 kmPEG-Lys(maleimide)-alkyne.

Figure 1B:
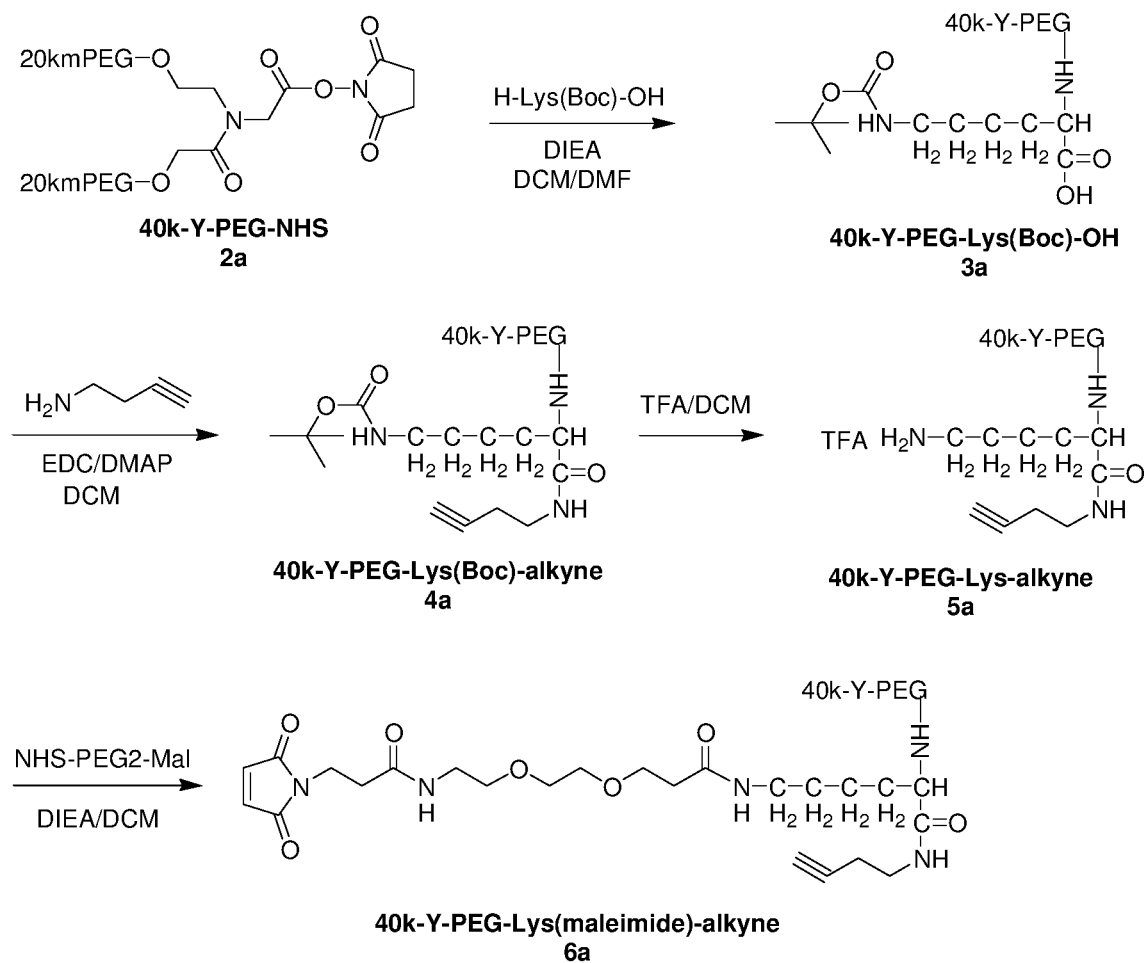
FIG. 1B schematically illustrates a reaction scheme of preparing 40k-Y-PEG-Lys(maleimide)-alkyne described in Example 2 (compounds 3a, 4a, 5a, 6a).

Example 2. Preparation of 40kY-PEG-Lys(maleimide)-alkyne (FIG. 1B)

Preparation of 40k-Y-PEG-Lys(Boc)-OH
(Compound 3a)

246 mg of H-lys(boc)-OH (4 eq.), 323 mg of DIEA (10 eq.) and 10 g of 40k-Y-PEG-NHS (1 eq.) were mixed in 100 mL DMF and 100 ml DCM. The mixture was stirred at room temperature overnight. The insoluble materials were filtered off. The solvent was removed and the residue was recrystallized from 2-propanol. The isolated product was dried at 40° C. under vacuum to yield 9.1 g of 40k-Y-PEG-Lys(Boc)-OH.

Preparation of 40k-Y-PEG-Lys(Boc)-alkyne
(Compound 4a)

9 g of 40k-Y-PEG-Lys(Boc)-OH (1 eq.) was dissolved in 90 mL of DCM and cooled to 0-5° C. 62.3 mg of 1-amino-3-butyne (4 eq.) was added followed by 247 mg of DMAP (9 eq.) and 259 mg of EDC (6 eq). The mixture was stirred at 0-5° C. for 1 hour. The cooling was removed and the reaction was left at room temperature overnight. Solvent was removed and the residue was recrystallized from 2-propanol. The isolated product was dried under vacuum at 40° C. to yield 8.4 g of 40k-Y-PEG-Lys(Boc)-alkyne.

Preparation of 40k-Y-PEG-Lys-alkyne (Compound 5a)

8.2 g of 40k-Y-PEG-lys(Boc)-alkyne was treated with 120 mL of TFA/DCM (1:2) at room temperature for 1 hr. Solvent was removed under vacuum. The residue was recrystallized from ethyl ether/DCM. The isolated product was dried under vacuum at 40° C. to yield 7.9 g of 40k-Y-PEG-Lys-alkyne.

Preparation of 40k-Y-PEG-Lys(maleimide)-alkyne
(Compound 6a)

7.68 g of 40k-Y-PEG-lys-alkyne (1 eq.) was dissolved in 80 mL of DCM. 495 mg of DIEA (20 eq) was added followed by 204 mg of NHS-PEG2-Mal (2.5 eq) at 0/5° C. The mixture was stirred at room temperature overnight. Solvent was removed and the residue was recrystallized from 2-propanol. The isolated product was dried under vacuum to yield 7.24 g of 40k-Y-PEG-Lys(maleimide)-alkyne.

Figure 1C:
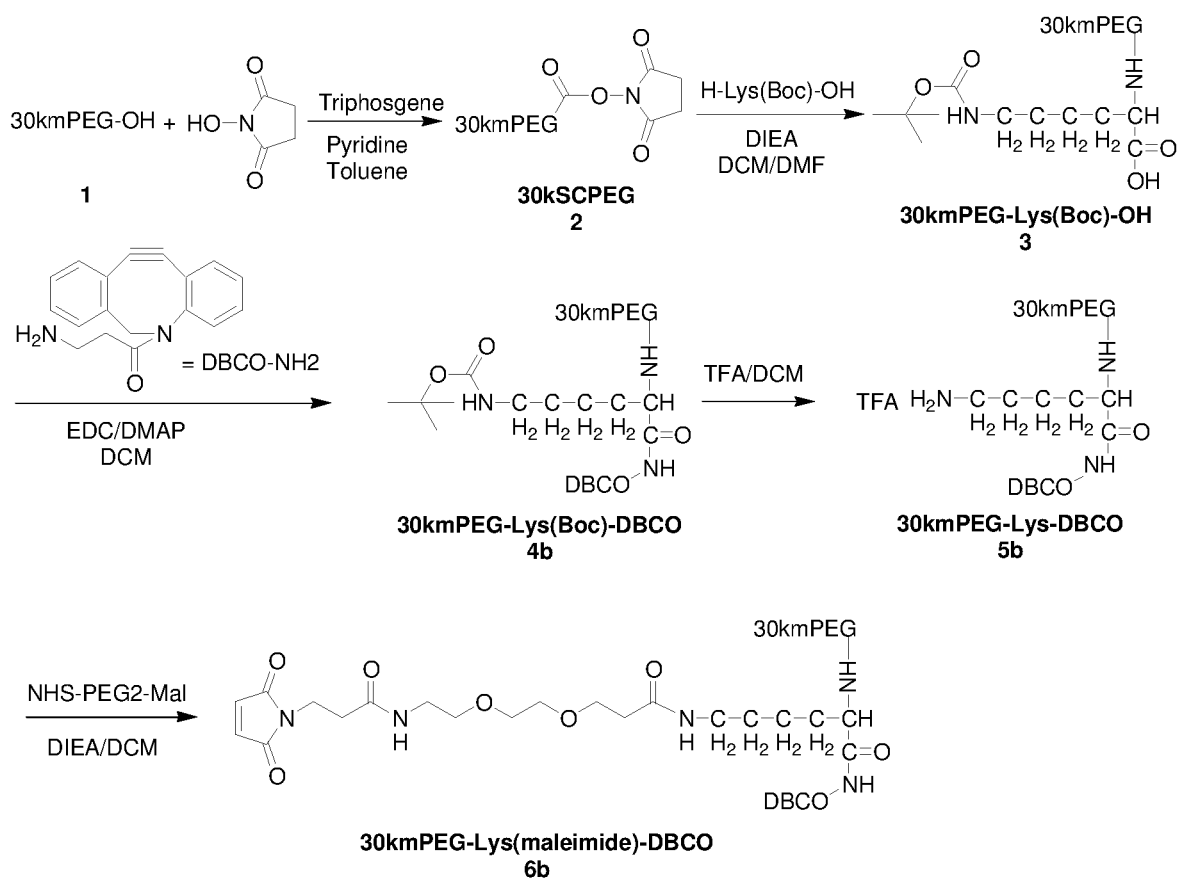
FIG. 1C schematically illustrates a reaction scheme of preparing 30 kmPEG-Lys(maleimide)-DBCO described in Example 3 (compounds 4b, 5b, 6b).

Example 3. Preparation of 30 kmPEG-Lys(maleimide)-DBCO (FIG. 1C)

Preparation of 30 kmPEG-Lys(Boc)-DBCO
(Compound 4b)

6 g of 30 kmPEG-Lys(Boc)-OH (1 eq.) was dissolved in 60 mL of DCM and cooled to 0-5° C. 221.1 mg of NH2-DBCO (4 eq.) was added followed by 219.6 mg of DMAP (9 eq.) and 230.4 mg of EDC (6 eq). The mixture was stirred at 0-5° C. for 1 hour. The cooling was removed and the reaction was left at room temperature room temperature overnight. Solvent was removed and the residue was recrystallized from 2-propanol. The isolated product was dried under vacuum at 40° C. to yield 5.7 g of 30 kmPEG-Lys(Boc)-alkyne.

Preparation of 30 kmPEG-Lys-DBCO (Compound 5b)

5.7 g of 30 kmPEG-lys(Boc)-DBCO was treated with 86 mL of TFA/DCM (1:2) at room temperature for 1 hr. Solvent was removed under vacuum. The residue was recrystallized from ethyl ether/DCM. The isolated product was dried under vacuum at 40° C. to yield 5.5 g of 30 kmPEG-Lys-alkyne.

Preparation of 30 kmPEG-Lys(maleimide)-DBCO
(Compound 6b)

5.5 g of 30 kmPEG-lys-DBCO (1 eq.) was dissolved in 55 mL of DCM. 473 mg of DIEA (20 eq) was added followed by 195 mg of NHS-PEG2-Mal (2.5 eq) at 0/5° C. The mixture was stirred at room temperature overnight. Solvent was removed and the residue was recrystallized from 2-propanol. The isolated product was dried under vacuum to yield 5.1 g of 30 kmPEG-Lys(maleimide)-DBCO.

Example 4. Preparation of SCACD3 and SCACD19

Single chain antibody (SCA) fragments anti-CD3 (SCACD3) and anti-CD19 (SCACD19) were made via recombinant DNA technology in *Pichia pastorius* using an EasySelect™ Pichia Expression Kit containing a pPICZ vector. Genes encoding anti-CD3 VH-VL and anti-CD19 VL-VH were synthesized and cloned into pPIZA expression vectors and transformed in a *P. pastoris* X33 strain. Expression of SCAs was induced by methanol and purified by Ni-chelating resin. To facilitate the subsequent conjugation, a site specific functional group thiol was inserted through recombinant DNA technology into the linker between VH and VL for both SCACD3 and SCACD19. Pure SCACD3 and SCADCD19 were obtained via chromatographic process. DNA Sequences of SCACD3 and SCACD19 were listed below.

```
DNA Sequence of SCACD3 in pUC57 (SEQ ID NO: 3):
  1 GACATCAAAC TGCAACAAAG CGGTGCTGAA CTGGCACGTC CGGGCGCATC CGTCAAAATG

61 AGCTGTAAGA CCTCGGGCTA TACCTTCACC CGTTACACGA TGCATTGGGT CAAGCAGCGT

121 CCGGGTCAAG GTCTGGAATG GATTGGTTAT ATCAACCCGT CTCGTGGCTA CACCAACTAC

181 AACCAGAAGT TCAAGGATAA GGCAACCCTG ACCACGGACA AAAGCTCTAG TACGGCTTAT

241 ATGCAACTGT CCTCACTGAC CTCTGAAGAT AGTGCGGTGT ATTACTGCGC CCGCTATTAC

301 GATGACCACT ATTGTCTGGA CTACTGGGGC CAGGGTACCA CGCTGACGGT GTCGAGCGTT

361 GAAGGCGGTT CCGGCGGTTC AGGCGGTTCG GGCGGTAGCG GCGGTGTTGA TGACATTCAG

421 CTGACCCAAT CACCGGCAAT CATGAGCGCT TCTCCGGGTG AAAAGGTTAC CATGACGTGC

481 CGTGCGTCTA GTTCCGTCAG TTATATGAAT TGGTACCAGC AAAAGTCTGG TACGAGTCCG

541 AAACGTTGGA TTTATGATAC CTCCAAAGTC GCAAGCGGTG TGCCGTACCG TTTCAGTGGT

601 TCCGGTTCAG GCACCTCGTA TAGCCTGACG ATCTCATCGA TGGAAGCCGA AGATGCGGCC

661 ACCTATTACT GTCAACAATG GAGTAGTAAC CCGCTGACCT TTGGCGCTGG CACGAAACTG

721 GAACTGAAAT GT

DNA Sequence SCACD19 in pUC57 (SEQ ID NO: 4):
  1 GACATTCAAC TGACGCAATC CCCGGCTTCC CTGGCGGTCT CGCTGGGTCA ACGCGCAACC

61 ATCTCGTGTA AAGCATCGCA ATCGGTCGAT TATGACGGCG ATTCCTATCT GAACTGGTAC

121 CAGCAAATTC CGGGTCAGCC GCCGAAGCTG CTGATCTACG ATGCGAGTAA TCTGGTCTCC

181 GGCATTCCGC CGCGTTTTTC CGGTTCAGGC TCGGGTACGG ACTTCACCCT GAACATCCAT

241 CCGGTGGAAA AAGTTGATGC GGCCACCTAT CACTGCCAGC AATCTACGGA AGACCCGTGG

301 ACCTTTGGCG GTGGCACGAA GCTGGAAATT AAAGGTGGCG GTGGCAGCGG TGGCGGTGGC

361 TCTGGTGGCG GTGGCAGTCA GGTGCAACTG CAGCAAAGCG GTGCAGAACT GGTCCGTCCG

421 GGTAGCTCTG TGAAGATCTC ATGTAAAGCA TCGGGCTATG CTTTCAGTTC CTACTGGATG

481 AATTGGGTTA ACAGCGCCC GGGCCAAGGT CTGGAATGGA TTGGTCAGAT CTGGCCGGGC

541 GACGGTGATA CCAACTACAA TGGCAAATTT AAGGGTAAAG CGACGCTGAC CGCCGATGAA

601 TCATCGAGCA CCGCATATAT GCAGCTGTCT AGTCTGGCAA GCGAAGACTC TGCTGTTTAC

661 TTCTGCGCAC GTCGCGAAAC CACGACCGTC GGTCGTTACT ACTACGCTAT GGACTATTGG

721 GGTCAAGGCA CCACCGTTAC CGTTTCAAGT TGC
```

Figure 2A:
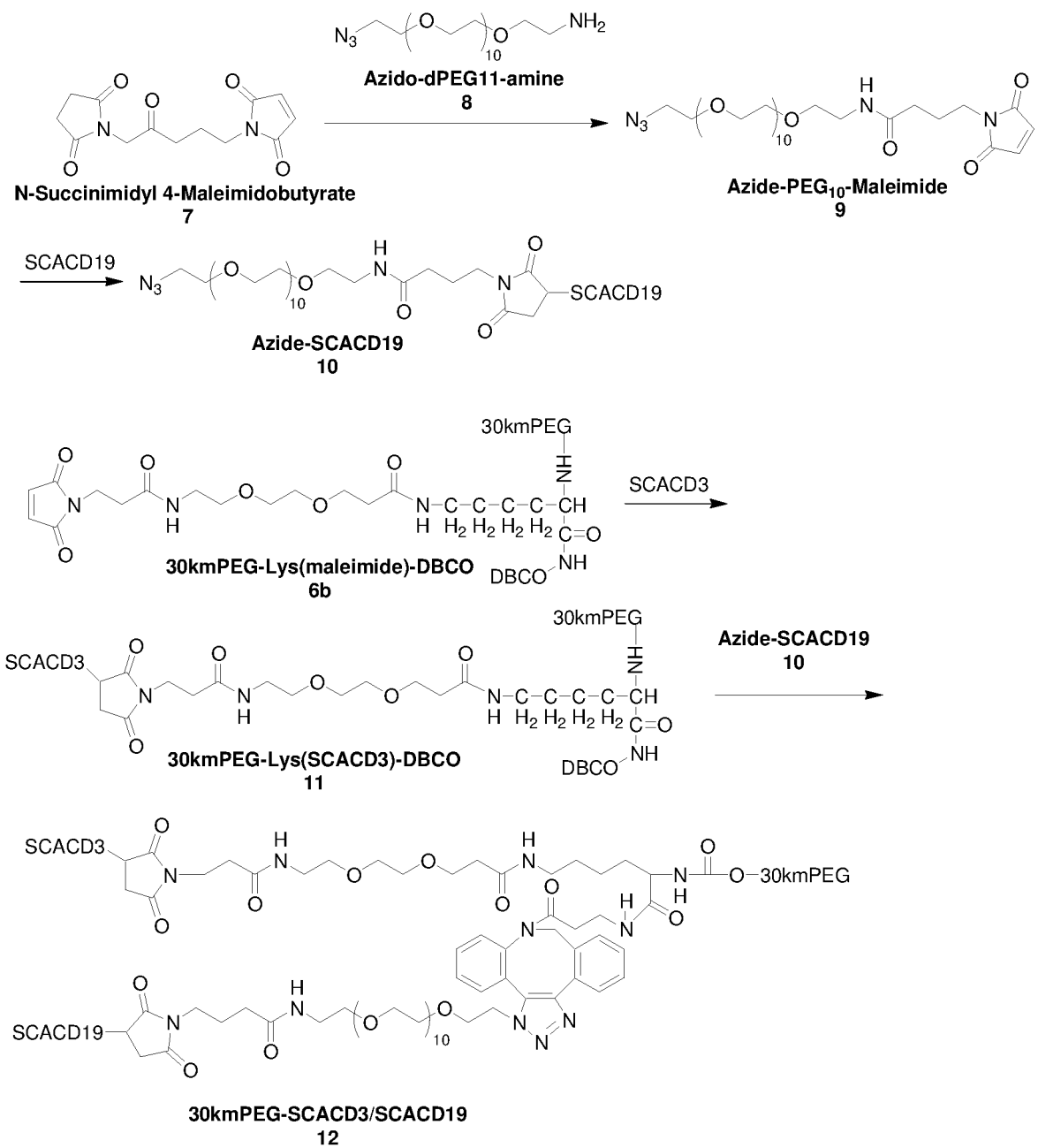
FIG. 2A schematically illustrates a reaction scheme of preparing PEGylated single chain antibody 30 kmPEG-SCACD3-SCACD19 with click chemistry without Cu catalyst described in Example 5 (compounds 9-12).

Example 5. Preparation of 30 kmPEG-(SCACD3)SCACD19 with Click Chemistry Without Cu Catalyst (FIG. 2A)

Preparation of Azide-PEG$_{10}$-Maleimide (Compound 9)

15 mg of N-Succinimidyl 4-Maleimidobutyrate (1 eq.) was reacted with 38 mg of Azido-dPEG$_{10}$-amine (1.5 eq.) in 200 µl DMSO at room temperature for 45 min. Resulting compound azide-PEG$_{10}$-Maleimide was used immediately at next step without further purification.

Preparation of Azide-SCACD19 (Compound 10)

31 mg of SCACD19 (1 eq.) (1-5 mg/ml) was reduced by 2-8 mM of TCEP-HCl in 20 mM Tris, 1.5% PEG600, pH8.0 for 30 min. The reduced SCADCD19 (1 eq.) was added to 200 µl of bifunctional linker Azide-PEG$_{10}$-Maleimide (50 eq.). The mixture was vertexed and left on shaker at room temperature for 3 hours. The reaction was quenched by 100

µl of 200 mM cysteine at room temperature for 10 min. Excess linkers Azide-PEG$_{10}$-Maleimide was removed by a desalting column HiPrep™ 26/10 (Cat #17-5087-01, GE Healthcare, NJ) with a buffer of 20 mM Tris, 1.5% PEG600, pH8.0, followed by a Capto™ Q (GE Healthcare, NJ) column. Fractions from Capt™ Q were collected and analyzed by SDS-PAGE stained by SimplerBlue™. Based on the SDS-PAGE profile, desired compound Azide-SCACD19 fractions were pooled, concentrated to 1-5 mg/ml and stored in a refrigerator for further use.

Preparation of 30 kmPEG-Lys(SCACD3)-DBCO (Compound 11)

24 mg of SCACD3 (1 eq.) (1-5 mg/ml) was reduced by 2-5 mM TCEP-HCl in 20 mM sodium phospahte, 1.5% PEG600, at pH6.0 for 30 min. The reduced 24 mg of SCADCD3 (1 eq) was mixed with 264 mg of 30 KmPEG-Lys(Maleimide)-DBCO (10 eq.) in 20 mM Na phosphate, 1.5% PEG600, pH6.0. The mixture was vertexed and left on shaker at room temperature for about 3 hours. The 30 kmPEG-Lys(SCACD3)-DBCO was purified by a 20 mL CM Sepgharose Fast Flow (GE Healthcare) column pre-equilibrated with 20 mM Na phosphate, 1.5% PEG600, pH6.0. After loading sample, the column was washed by 10 CV of equilibration buffer to wash off free PEGs completely, then eluted by 0.5 M NaCl. Fractions were collected and analyzed by SDS-PAGE stained by SimplerBlue™ and iodine. Based on the SDS-PAGE profile, 30 kmPEG-Lys (SCACD3)-DBCO was pooled and concentrated to 1-5 mg/ml. The buffer was exchanged to PBS for further use.

Preparation of 30 kmPEG-SCACD3/SCACD19 (Compound 12)

Conjugation of 30 kmPEG-Lys(SCACD3)-DBCO (compound 11) with Azide-SCACD19 (compound 10) was achieved by a clicking chemistry at 1:1 mole ratio in PBS at room temperature overnight. Purification of target PEGFyalted bispecific antibody 30 kmPEG-SCACD3/SCACD19 was performed first by a HiPrep™ 26/10 Desalting Column with a 20 mM Tris, pH8.0 buffer, followed by DEAE Fast Flow Sepharose (GE Healthcare, NJ) and CM Fast Flow Sepharose (GE Healthcare). All column chromatographic purifications were run similarly to the procedures described above. Fractions were collected and analyzed by SDS-PAGE stained by SimplerBlue™ and iodine. Based on the SDS-PAGE profile, final bispecific antibody product was pooled and concentrated to ~1 mg/ml in PBS, pH7.4. The target compound was confirmed by SEC-HPLC and cell based activity assay.

Figure 2B:
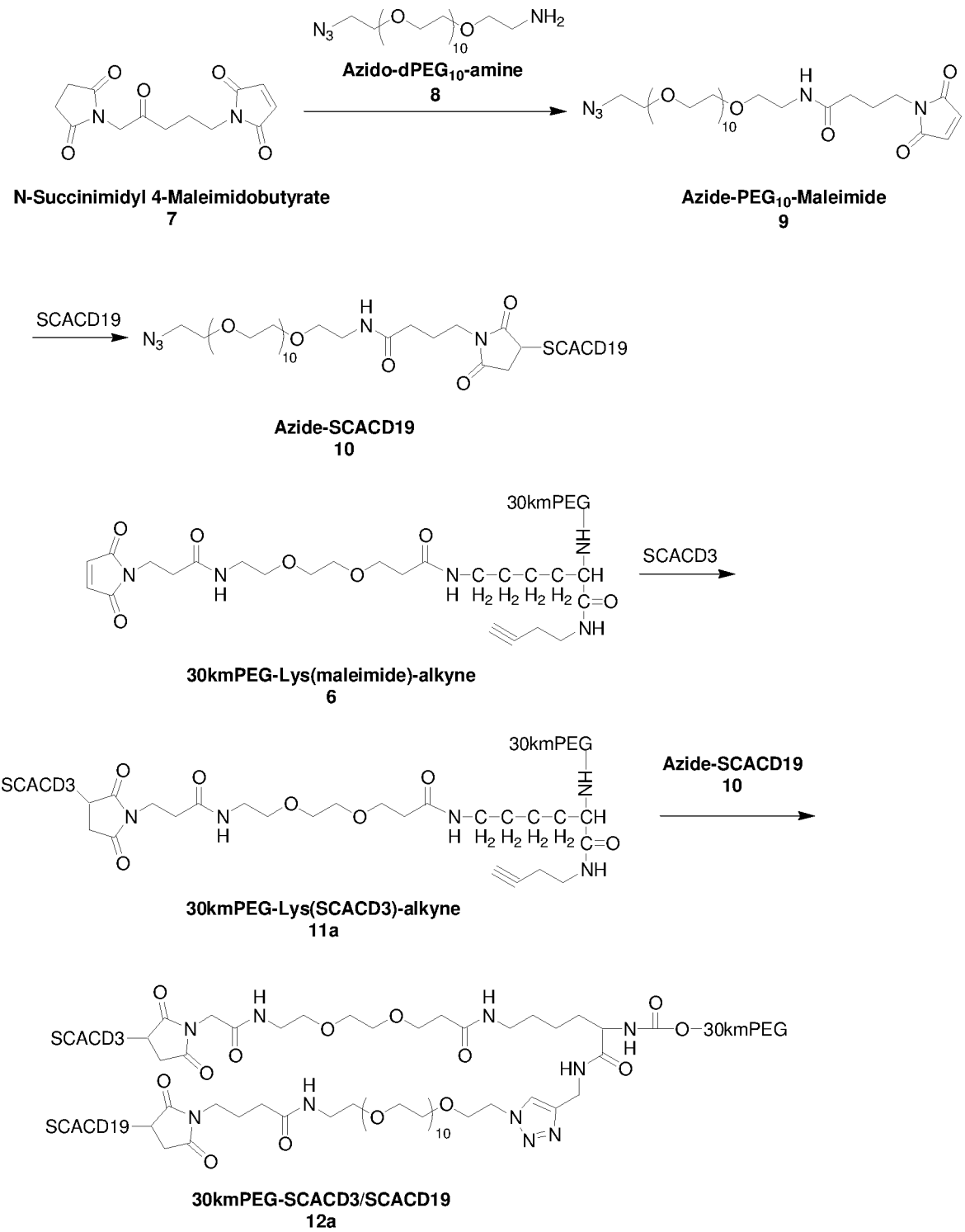
FIG. 2B schematically illustrates a reaction scheme of preparing PEGylated single chain antibody 30 kmPEG-SCACD3-SCACD19 with click chemistry with Cu catalyst described in Example 6 (compounds 11a-12a).

Example 6. Preparation of 30 kmPEG-(SCACD3) SCACD19 with Click Chemistry with Cu Catalyst (FIG. 2B)

Preparation of 30 kmPEG-Lys(SCACD3)-Alkyne (Compound 11a)

24 mg of SCACD3 (1 eq.) (1-5 mg/ml) was reduced by 2-5 mM TCEP-HCl in 20 mM sodium phospahte, 1.5% PEG600, at pH6.0 for 30 min. The reduced 24 mg of SCADCD3 (1 eq) was mixed with 264 mg of 30 KmPEG-Lys(Maleimide)-Alkyne (10 eq.) in 20 mM Na phosphate, 1.5% PEG600, pH6.0. The mixture was vertexed and left on shaker at room temperature for about 3 hours. The 30 kmPEG-Lys(SCACD3)-Alkyne (compound 11a) was puri- fied by a 20 mL CM Sepgharose Fast Flow (GE Healthcare) column in equilibrated with 20 mM, Na phosphate, 1.5% PEG600, pH6.0. After loading sample, the column was washed by 10 CV equilibration buffer to wash off free PEGs completely, then eluted by 0.5 M NaCl. Fractions were collected and analyzed by SDS-PAGE stained by SimplerBlue™ and iodine. Based on the SDS-PAGE profile, 30 kmPEG-Lys(SCACD3)-Alkyne was pooled and concentrated to 1-5 mg/ml. The buffer was exchanged to PBS for further use.

Preparation of 30 kmPEG-SCACD3/SCACD19 (Compound 12a)

Conjugation of 30 kmPEG-Lys(SCACD3)-Alkyne (compound 11a) with Azide-SCACD19 (compound 10) was achieved by a clicking chemistry at 1:1 mole ratio in PBS at room temperature overnight at presence of 15 µM Cu(I) and 30 µM of Tis(benzyltrialzolylmethyl)$_a$mine (TBTA) (pre-prepared in DMSO).

Purification of target PEGFyalted bispecific antibody 30 kmPEG-SCACD3/SCACD19 (compound 12a) was performed similarly as described for compound 12 in Example 5.

Figure 3:
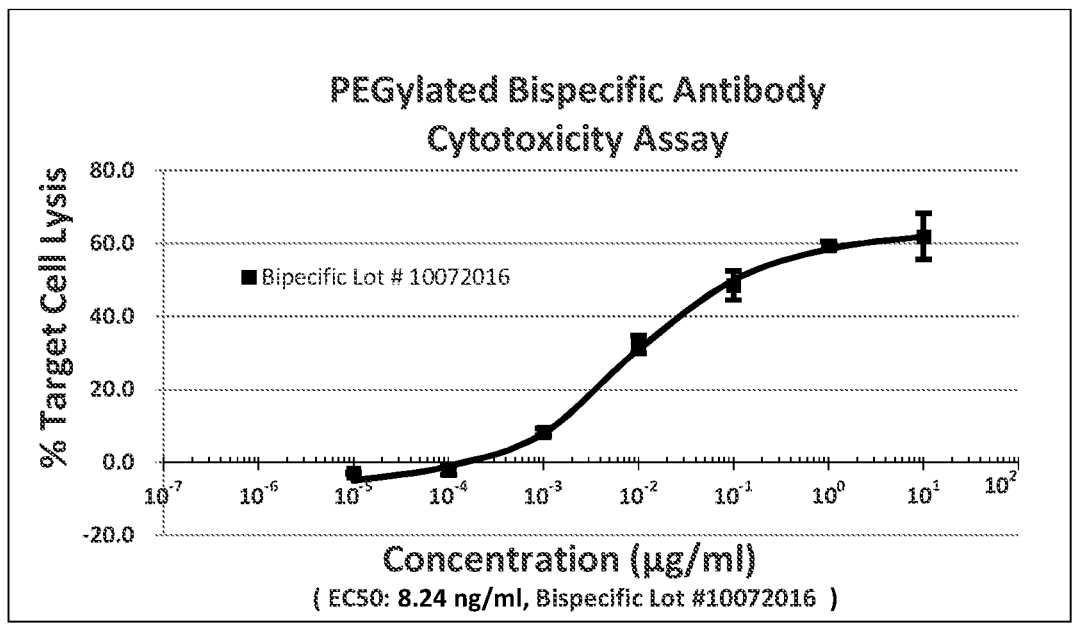
FIG. 3 in-vitro T cell mediated cytotoxicity described in Example 7.
Figure 4:
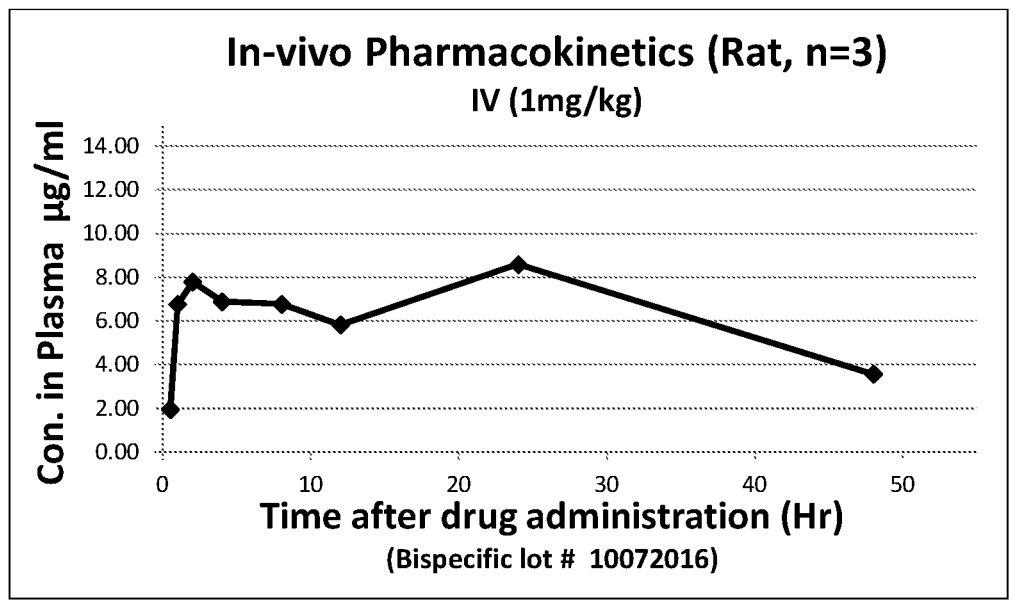
FIG. 4 in-vivo pharmacokinetics described in Example 7.

Example 7. Biological Data (FIGS. 3 and 4)

In-Vitro T Cell Mediated Cytotoxicity

In vitro bscCD19xCD3 cytotoxicity assay was performed to evaluate the cytotoxicity potency of PEGyalted bispecific antibody compound 12. This study was used to demonstrate that DSP-BsAb technology is an alternative technology for preparing bispecific antibodies, which are able to recruit effector cells to destroy the cancer cells for onco-immunotherapy. The cytotoxicity of compound 12 was determined using a color metric LDH release assay. Half maximal effective concentration ($EC_{50}$) values were analyzed with the 4 parameter logistic non-linear regression model fit by GraphPad Prism 6.

Briefly, for this study, the target Raji cell (B lymphoma cell line) maintained in a complete medium at 37° C./5% $CO_2$ were incubated with compound 12 (diluted with Phenol red free MEM medium supplemented with 1% FBS before addition) at different concentrations for 0.5 hours at 37° C. CD8$^+$ T cells isolated from PBMCs (from 20 healthy individuals) by a CD8$^+$ T Cell Isolation Kit were added as effector cells (E:T ratio=5:1). The mixtures of compound 12, Raji cell and effector cells were further incubated at 37° C./5% $CO_2$ for 24 hours. The supernatants were collected for assaying the cell viability with a LDH kit. The absorbance data at $OD_{492\ nm}$ and $OD_{650\ nm}$ were read. $OD_{492\ nm}$ data subtracted the background ($OD_{650\ nm}$) were analyzed to study the LDH release. The percentages of cell lysis were calculated according the formula below:

$$\text{Cell lysis \%} = 100 * (OD_{Sample\ data} - OD_{target\ cells\ plus\ effector\ cells}) / (OD_{Maximum\ release} - OD_{Minimum\ release})$$

The results (average±SD, (n=3)) were shown in FIG. 3. The analysis data was listed in Table 1. The $EC_{50}$ value of 8.24 ng/ml indicated that the compound 12 is significantly cytotoxic toward the target cells. In addition, the compound 12 has also shown dose-dependent killing power toward the target cells.

TABLE 1

Best fit values summary for in vitro
bscCD19xCD3 Cytotoxicity Assay

| | Bispecific Lot 10072016 |
|---|---|
| Bottom | −5.225 |
| Top | 62.33 |
| LogEC$_{50}$ | −2.084 |
| Hill Slop | 0.6166 |
| EC$_{50}$ µg/ml | 0.008237 |

In-Vivo Pharmacokinetics

This study was designed to demonstrate that DSP-BsAb technology disclosed here can dramatically extend the elimination half life of a traditional single chain bispecific antibody. The pharmacokinetics of the PEGyalted single chain bispecific antibody was determined after intravenous injection of 1 mg/kg into rats. Because the half life of PEGylated conjugates in rats are typically in the range of 5 times shorter than in humans, the half life of a PEGylated single chain bispecific antibody in rats in this study should reach about 10 hours or longer for possible weekly drug administration in human.

For the study, the experiment was conducted as follows: tumor free Sprague-Dawley male rats (about 250 g, n=3) were fitted with two jugular vein cannula (JVC). Food was withheld from the animals for a minimum of twelve hours prior to drug administration until four hours post dose. Water was offered ad libitum. The rats were injected intravenously via the JVC with a single injection of 1 mg/kg bispecific antibody compound 12. At various time points (Pre-dose, 30 min, 1, 2, 4, 8, 12, 24 and 48 hours), about 0.3 ml blood samples were taken either from jugular vein cannula or tail vein and placed into chilled tubes containing sodium heparin. The samples were centrifuged at 4° C. and plasmas were collected and frozen until assayed.

Pharmacokinetic analysis was carried out by using ELISA assay. Briefly, a microplate was coated with CD19 antigens overnight at 2-8° C. first, while any nonspecific binding sites on the surface were blocked with 2% BSA in PBS. Plates were washed 3×5 min with PBS, 0.05% v/v Tween20, before rat plasma samples were applied. After 1.5 hours incubation at 37° C., the plates were washed 3×5 min with PBS, 0.05% v/v Tween20 followed by anti-PEG antibodies binding at 37° C. for 1 hour. The plates were washed 3×5 min with PBS, 0.05% v/v Tween20 before enzyme-linked antibodies were applied. The plates were then treated with enzyme substrates to develop color and stopped by 1 N of sulfuric acid. The plasma concentrations of the compound 12 were calculated from a calibration curve and plotted against time. The results show (FIG. 4 and Table 2) that the compound 12 provides much longer elimination half life ($T_{1/2}$=27.48 hours) in rat than blinatumomab ($t_{1/2}$<0.5 hour), which is a non-PEGylated version of the single chain CD19/CD3 bispecific antibody.

TABLE 2

Pharmacokinetic Analysis

| | |
|---|---|
| Dose per animal | 0.25 mg/animal |
| Volume distribution, Vd | 128.2 mL/kg |
| AUC | 309.2 h * ug/mL |
| Clearance, CL | 3.24 mL/h · kg |
| $T_{1/2}$ | 27.48 hours |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference herein in their entireties.

What is claimed is:

1. A compound of the Formula Ib:

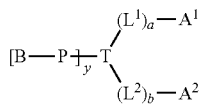

wherein:

P is a polyethylene glycol (PEG);

B is H, a terminal capping group or void, said capping group selected from $C_{1-50}$ alkyl and aryl, wherein one or more carbons of said alkyl may be replaced with a heteroatom;

T is a tri-functional linker, wherein the linkage between T and $(L^1)_a$ and the linkage between T and $(L^2)_b$ are the same or different; wherein said linkage between T and $(L^1)_a$ or T and $(L^2)_b$ is derived from hydroxyl, amino, hydrazinyl, carboxyl, thiol, halide, alkene, anhydride, or maleimide; or combinations thereof;

each of $L^1$ and $L^2$ is independently a bifunctional linker;

a and b are each an integer selected from 1 to 10;

one of $A^1$ and $A^2$ is a protein encoded by SCACD3 (SEQ ID No: 3) and the other is a protein encoded by SCACD19 (SEQ ID No. 4); and y is 1.

2. The compound of claim 1, wherein the PEG is a linear PEG.

3. The compound of claim 1, wherein the PEG is a branched PEG.

4. The compound of claim 1, wherein at least one terminal or branch of the PEG is capped with methyl or a low molecule weight alkyl group.

5. The compound of claim 1, wherein the total molecule weight of the PEG is 3,000 to 100,000.

6. The compound of claim 1, wherein the PEG is linked to a trifunctional moiety through a permanent bond.

7. The compound of claim 1, wherein $(L^1)_a$ and/or $(L^2)_b$ independently comprise one or more bifunctional linkages formed from one or more functional groups selected from the group consisting of thiol, maleimide, aromatic or vinyl sulfone, acrylate, bromo or iodo acetamide, azide, alkyne, dibenzocyclooctyl (DBCO), carbonyl, 2-amino-benzaldehyde or 2-amino-acetophenone group, hydrazide, oxime, potassium acyltrifluoroborate, O-carbamoylhydroxylamine, trans-cyclooctene, tetrazine, and triarylphosphine.

8. A pharmaceutical formulation comprising the compound of claim 1 and a pharmaceutically acceptable carrier.

9. The compound of claim 7, wherein one of $(L^1)_a$ and $(L^2)_b$ comprises a linkage formed from azide and alkyne.

10. The compound of claim 9, wherein the other of the $(L^1)_a$ and $(L^2)_b$ comprises a linkage formed from maleimide and thiol.

11. The compound of claim 9, wherein the alkyne is dibenzocyclooctyl (DBCO).

12. The compound of claim 1, wherein T is derived from lysine.

13. The compound of claim 1, wherein T is derived from lysine, 1,3-diamino-2-propanol, or triethanolamine.

14. The compound of claim 1, wherein $(L^1)_a$ and/or $(L^2)_b$ independently comprise $-(CH_2)_mO(CH_2CH_2O)_n-$.

* * * * *

SEQUENCE LISTING

```
<160> NUMBER OF SEQ ID NOS: 4

<210> SEQ ID NO 1
<211> LENGTH: 244
<212> TYPE: PRT
<213> ORGANISM: Artificial Sequence
<220> FEATURE:
<223> OTHER INFORMATION: single chain antibody Fv

<400> SEQUENCE: 1

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95
```

```
Ala Arg Tyr Tyr Asp Asp His Tyr Cys Leu Asp Tyr Trp Gly Gln Gly
            100                 105                 110

Thr Thr Leu Thr Val Ser Ser Val Glu Gly Cys Gly Ser Gly Gly Ser
        115                 120                 125

Gly Gly Ser Gly Gly Ser Gly Gly Val Asp Asp Ile Gln Leu Thr Gln
        130                 135                 140

Ser Pro Ala Ile Met Ser Ala Ser Pro Gly Glu Lys Val Thr Met Thr
145                 150                 155                 160

Cys Arg Ala Ser Ser Ser Val Ser Tyr Met Asn Trp Tyr Gln Gln Lys
                165                 170                 175

Ser Gly Thr Ser Pro Lys Arg Trp Ile Tyr Asp Thr Ser Lys Val Ala
            180                 185                 190

Ser Gly Val Pro Tyr Arg Phe Ser Gly Ser Gly Ser Gly Thr Ser Tyr
        195                 200                 205

Ser Leu Thr Ile Ser Ser Met Glu Ala Glu Asp Ala Ala Thr Tyr Tyr
        210                 215                 220

Cys Gln Gln Trp Ser Ser Asn Pro Leu Thr Phe Gly Ala Gly Thr Lys
225                 230                 235                 240

Leu Glu Leu Lys

<210> SEQ ID NO 2
<211> LENGTH: 250
<212> TYPE: PRT
<213> ORGANISM: Artificial Sequence
<220> FEATURE:
<223> OTHER INFORMATION: single chain antibody Fv

<400> SEQUENCE: 2

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Cys Gly Gly Gly Ser Gly Gly Gly Gly Ser Gly Gly Gly Gly Ser Gln
        115                 120                 125

Val Gln Leu Gln Gln Ser Gly Ala Glu Leu Val Arg Pro Gly Ser Ser
        130                 135                 140

Val Lys Ile Ser Cys Lys Ala Ser Gly Tyr Ala Phe Ser Ser Tyr Trp
145                 150                 155                 160

Met Asn Trp Val Lys Gln Arg Pro Gly Gln Gly Leu Glu Trp Ile Gly
                165                 170                 175

Gln Ile Trp Pro Gly Asp Gly Asp Thr Asn Tyr Asn Gly Lys Phe Lys
            180                 185                 190

Gly Lys Ala Thr Leu Thr Ala Asp Glu Ser Ser Ser Thr Ala Tyr Met
        195                 200                 205

Gln Leu Ser Ser Leu Ala Ser Glu Asp Ser Ala Val Tyr Phe Cys Ala
```

```
            210                 215                 220
Arg Arg Glu Thr Thr Val Gly Arg Tyr Tyr Tyr Ala Met Asp Tyr Trp
225                 230                 235                 240

Gly Gln Gly Thr Thr Val Thr Val Ser Ser
                245                 250

<210> SEQ ID NO 3
<211> LENGTH: 732
<212> TYPE: DNA
<213> ORGANISM: Artificial Sequence
<220> FEATURE:
<223> OTHER INFORMATION: Single chain antibody (SCA) fragment

<400> SEQUENCE: 3
gacatcaaac tgcaacaaag cggtgctgaa ctggcacgtc cgggcgcatc cgtcaaaatg      60
agctgtaaga cctcgggcta taccttcacc cgttacacga tgcattgggt caagcagcgt     120
ccgggtcaag gtctggaatg gattggttat atcaacccgt ctcgtggcta caccaactac     180
aaccagaagt tcaaggataa ggcaaccctg accacggaca aaagctctag tacggcttat     240
atgcaactgt cctcactgac ctctgaagat agtgcggtgt attactgcgc ccgctattac     300
gatgaccact attgtctgga ctactggggc caggtaccag cgctgacggt gtcgagcgtt     360
gaaggcggtt ccggcggttc aggcggttcg ggcggtagcg gcggtgttga tgacattcag     420
ctgacccaat caccggcaat catgagcgct tctccgggtg aaaaggttac catgacgtgc     480
cgtgcgtcta gttccgtcag ttatatgaat tggtaccagc aaaagtctgg tacgagtccg     540
aaacgttgga tttatgatac ctccaaagtc gcaagcggtg tgccgtaccg tttcagtggt     600
tccggttcag gcacctcgta tagcctgacg atctcatcga tggaagccga agatgcggcc     660
acctattact gtcaacaatg gagtagtaac ccgctgacct tggcgctggg cacgaaactg     720
gaactgaaat gt                                                         732

<210> SEQ ID NO 4
<211> LENGTH: 753
<212> TYPE: DNA
<213> ORGANISM: Artificial Sequence
<220> FEATURE:
<223> OTHER INFORMATION: Single chain antibody (SCA) fragment

<400> SEQUENCE: 4
gacattcaac tgacgcaatc cccggcttcc ctggcggtct cgctgggtca acgcgcaacc      60
atctcgtgta agcatcgca atcggtcgat tatgacggcg attcctatct gaactggtac     120
cagcaaattc cgggtcagcc gccgaagctg ctgatctacg atgcgagtaa tctggtctcc     180
ggcattccgc gcgttttttc cggttcaggc tcgggtacgg acttcaccct gaacatccat     240
ccggtggaaa aagttgatgc ggccacctat cactgccagc aatctacgga agacccgtgg     300
acctttggcg gtggcacgaa gctggaaatt aaaggtggcg gtggcagcgg tggcggtggc     360
tctggtggcg gtggcagtca ggtgcaactg cagcaaagcg gtgcagaact ggtccgtccg     420
ggtagctctg tgaagatctc atgtaaagca tcgggctatg ctttcagttc ctactggatg     480
aattgggtta acagcgcccc gggccaaggt ctggaatgga ttggtcagat ctggccgggc     540
gacggtgata ccaactacaa tggcaaattt aagggtaaag cgacgctgac cgccgatgaa     600
```

| | |
|---|---|
| tcatcgagca ccgcatatat gcagctgtct agtctggcaa gcgaagactc tgctgtttac | 660 |
| ttctgcgcac gtcgcgaaac cacgaccgtc ggtcgttact actacgctat ggactattgg | 720 |
| ggtcaaggca ccaccgttac cgtttcaagt tgc | 753 |